(12) United States Patent
Rice et al.

(10) Patent No.: US 11,331,018 B2
(45) Date of Patent: May 17, 2022

(54) SYSTEM AND SINGLE-CHANNEL BIOSENSOR FOR AND METHOD OF DETERMINING ANALYTE VALUE

(71) Applicant: Profusa, Inc., South San Francisco, CA (US)

(72) Inventors: Brad Rice, South San Francisco, CA (US); Soya Gamsey, San Francisco, CA (US); William A. McMillan, La Honda, CA (US)

(73) Assignee: Profusa, Inc., Emeryville, CA (US)

( * ) Notice: Subject to any disclaimer, the term of this patent is extended or adjusted under 35 U.S.C. 154(b) by 372 days.

(21) Appl. No.: 15/852,885

(22) Filed: Dec. 22, 2017

(65) Prior Publication Data

US 2018/0177443 A1 Jun. 28, 2018

Related U.S. Application Data

(60) Provisional application No. 62/438,113, filed on Dec. 22, 2016.

(51) Int. Cl.
*A61B 5/1455* (2006.01)
*A61B 5/145* (2006.01)
*A61B 5/1459* (2006.01)

(52) U.S. Cl.
CPC ........ *A61B 5/14556* (2013.01); *A61B 5/1459* (2013.01); *A61B 5/14532* (2013.01);
(Continued)

(58) Field of Classification Search
None
See application file for complete search history.

(56) References Cited

U.S. PATENT DOCUMENTS 4,703,756 A 11/1987 Gough et al.
5,001,054 A 3/1991 Wagner
(Continued)

FOREIGN PATENT DOCUMENTS

CN 1675547 A 9/2005
CN 1882278 A 12/2006
(Continued)

OTHER PUBLICATIONS

International Search Report and Written Opinion for International Application No. PCT/US2017/068201, dated Feb. 22, 2018, 11 pages.
(Continued)

*Primary Examiner* — Marjan Fardanesh
(74) *Attorney, Agent, or Firm* — Cooley LLP

(57) ABSTRACT

Some embodiments described herein relate to a sensor that includes an analyte-sensing dye and a reference dye. The analyte-sensing dye can be configured to emit an analyte-dependent optical signal in the presence of an analyte. Similarly stated, the intensity and/or duration of the analyte-dependent optical signal can be modulated by a quantity and/or concentration of the analyte in the environment of the sensor. The reference dye can be configured to emit an analyte-independent optical signal. The analyte-dependent optical signal and the analyte-independent optical signal have an analyte-dependent spectrum and an analyte-independent spectrum, respectfully. The analyte-dependent optical spectrum and the analyte-independent spectrum can be the same, substantially the same, and/or overlapping. The analyte-dependent optical signal can have a duration of lifetime that is shorter than a duration or lifetime of the analyte-independent optical signal.

20 Claims, 10 Drawing Sheets

(52) U.S. Cl.
CPC ...... *A61B 5/14539* (2013.01); *A61B 5/14546* (2013.01); *A61B 2562/0238* (2013.01)

(56) References Cited

U.S. PATENT DOCUMENTS

| | | | |
|---|---|---|---|
| 5,094,958 A | 3/1992 | Klainer et al. | |
| 5,161,532 A | 11/1992 | Joseph | |
| 5,284,140 A | 2/1994 | Allen et al. | |
| 5,342,789 A | 8/1994 | Chick et al. | |
| 5,462,880 A | 10/1995 | Kane et al. | |
| 5,512,246 A | 4/1996 | Russell et al. | |
| 5,551,422 A | 9/1996 | Simonsen et al. | |
| 5,777,060 A | 7/1998 | Van Antwerp | |
| 5,895,658 A | 4/1999 | Fossel | |
| 6,002,954 A | 12/1999 | Van Antwerp et al. | |
| 6,011,984 A | 1/2000 | Van Antwerp et al. | |
| 6,013,122 A | 1/2000 | Klitzman et al. | |
| 6,040,194 A | 3/2000 | Chick et al. | |
| 6,175,752 B1 | 1/2001 | Say et al. | |
| 6,212,416 B1 | 4/2001 | Ward et al. | |
| 6,299,604 B1 | 10/2001 | Ragheb et al. | |
| 6,319,540 B1 | 11/2001 | Van Antwerp et al. | |
| 6,376,971 B1 | 4/2002 | Pelrine et al. | |
| 6,379,622 B1 | 4/2002 | Polak et al. | |
| 6,475,750 B1 | 11/2002 | Han et al. | |
| 6,485,703 B1 | 11/2002 | Cote et al. | |
| 6,497,729 B1 | 12/2002 | Moussy et al. | |
| 6,543,110 B1 | 4/2003 | Pelrine et al. | |
| 6,565,509 B1 | 5/2003 | Say et al. | |
| 6,565,960 B2 | 5/2003 | Koob et al. | |
| 6,583,533 B2 | 6/2003 | Pelrine et al. | |
| 6,602,678 B2 | 8/2003 | Kwon et al. | |
| 6,602,716 B1 | 8/2003 | Klimant | |
| 6,642,015 B2 | 11/2003 | Vachon et al. | |
| 6,671,527 B2 | 12/2003 | Petersson et al. | |
| 6,702,857 B2 | 3/2004 | Brauker et al. | |
| 6,750,311 B1 | 6/2004 | Van Antwerp et al. | |
| 6,766,183 B2 | 7/2004 | Walsh et al. | |
| 6,794,195 B2 | 9/2004 | Colvin, Jr. | |
| 6,804,544 B2 | 10/2004 | Van Antwerp et al. | |
| 6,818,226 B2 | 11/2004 | Reed et al. | |
| 6,821,530 B2 | 11/2004 | Koob et al. | |
| 6,844,023 B2 | 1/2005 | Schulman et al. | |
| 6,858,184 B2 | 2/2005 | Pelrine et al. | |
| 6,916,660 B2 | 7/2005 | Wang et al. | |
| 6,927,246 B2 | 8/2005 | Noronha et al. | |
| 6,965,791 B1 | 11/2005 | Hitchcock et al. | |
| 6,994,691 B2 | 2/2006 | Ejlersen | |
| 7,045,361 B2 | 5/2006 | Heiss et al. | |
| 7,060,503 B2 | 6/2006 | Colvin, Jr. | |
| 7,067,194 B2 | 6/2006 | Mao et al. | |
| 7,110,803 B2 | 9/2006 | Shults et al. | |
| 7,132,049 B2 | 11/2006 | Hou et al. | |
| 7,134,999 B2 | 11/2006 | Brauker et al. | |
| 7,153,265 B2 | 12/2006 | Vachon | |
| 7,162,289 B2 | 1/2007 | Shah et al. | |
| 7,186,789 B2 | 3/2007 | Hossainy et al. | |
| 7,192,450 B2 | 3/2007 | Brauker et al. | |
| 7,202,947 B2 | 4/2007 | Liu et al. | |
| 7,226,978 B2 | 6/2007 | Tapsak et al. | |
| 7,228,159 B2 | 6/2007 | Petersson et al. | |
| 7,406,345 B2 | 7/2008 | Muller et al. | |
| 7,424,317 B2 | 9/2008 | Parker et al. | |
| 7,450,980 B2 | 11/2008 | Kawanishi | |
| 7,468,575 B2 | 12/2008 | Pelrine et al. | |
| 7,496,392 B2 | 2/2009 | Alarcon et al. | |
| 7,521,019 B2 | 4/2009 | Polak et al. | |
| 7,541,598 B2 | 6/2009 | Aasmul | |
| 7,567,347 B2 | 7/2009 | Aasmul | |
| 7,629,172 B2 | 12/2009 | Alarcon et al. | |
| 7,653,424 B2 | 1/2010 | March | |
| 7,704,704 B2 | 4/2010 | Ibey et al. | |
| 7,772,286 B2 | 8/2010 | Muller et al. | |
| 7,869,853 B1 | 1/2011 | Say et al. | |
| 7,923,064 B2 | 4/2011 | Pelrine et al. | |
| 7,927,519 B2 | 4/2011 | Domschke et al. | |
| 7,939,332 B2 | 5/2011 | Colvin, Jr. | |
| 7,972,628 B2 | 7/2011 | Ratner et al. | |
| 8,008,088 B2 | 8/2011 | Bellott et al. | |
| 8,024,020 B2 | 9/2011 | Rosero | |
| 8,057,041 B2 | 11/2011 | Muller et al. | |
| 8,088,595 B2 | 1/2012 | Ibey et al. | |
| 8,131,333 B2 | 3/2012 | Chapoy et al. | |
| 8,206,622 B2 | 6/2012 | Kammermeier et al. | |
| 8,318,193 B2 | 11/2012 | Ratner et al. | |
| 8,346,337 B2 | 1/2013 | Heller et al. | |
| 8,346,363 B2 | 1/2013 | Darvish et al. | |
| 8,368,556 B2 | 2/2013 | Sicurello et al. | |
| 8,372,423 B2 | 2/2013 | Marshall et al. | |
| 8,372,630 B2 | 2/2013 | Uematsu et al. | |
| 8,382,700 B2 | 2/2013 | Straessler et al. | |
| 8,385,998 B2 | 2/2013 | Zhang et al. | |
| 8,423,114 B2 | 4/2013 | Simpson et al. | |
| 8,452,361 B2 | 5/2013 | Muller | |
| 8,452,363 B2 | 5/2013 | Muller et al. | |
| 8,460,231 B2 | 6/2013 | Brauker et al. | |
| 8,465,425 B2 | 6/2013 | Heller et al. | |
| 8,483,793 B2 | 7/2013 | Simpson et al. | |
| 8,508,109 B2 | 8/2013 | Pelrine et al. | |
| 8,512,245 B2 | 8/2013 | Markle et al. | |
| 8,527,025 B1 | 9/2013 | Shults et al. | |
| 8,527,026 B2 | 9/2013 | Shults et al. | |
| 8,535,262 B2 | 9/2013 | Markle et al. | |
| 8,543,182 B2 | 9/2013 | Botvinick et al. | |
| 8,543,184 B2 | 9/2013 | Boock et al. | |
| 8,543,354 B2 | 9/2013 | Luo et al. | |
| 8,579,879 B2 | 11/2013 | Palerm et al. | |
| 8,608,924 B2 | 12/2013 | Cooper et al. | |
| RE44,695 E | 1/2014 | Simpson et al. | |
| 8,622,903 B2 | 1/2014 | Jin et al. | |
| 8,623,639 B2 | 1/2014 | Amiss et al. | |
| 8,628,471 B2 | 1/2014 | Mazar et al. | |
| 8,647,271 B2 | 2/2014 | Muller et al. | |
| 8,647,393 B2 | 2/2014 | Marshall et al. | |
| 8,666,471 B2 | 3/2014 | Rogers | |
| 8,927,022 B2 | 1/2015 | Maginness et al. | |
| 8,940,544 B2 | 1/2015 | Suri et al. | |
| 8,945,942 B2 | 2/2015 | Herbrechtsmeier et al. | |
| 9,244,064 B2 | 1/2016 | Muller et al. | |
| 9,826,926 B2 | 11/2017 | Muller et al. | |
| 2002/0043651 A1 | 4/2002 | Darrow et al. | |
| 2002/0048577 A1 | 4/2002 | Bornstein et al. | |
| 2002/0050769 A1 | 5/2002 | Pelrine et al. | |
| 2002/0094526 A1 | 7/2002 | Bayley et al. | |
| 2002/0106314 A1 | 8/2002 | Pelrine et al. | |
| 2002/0151772 A1 | 10/2002 | Polak | |
| 2002/0193672 A1 | 12/2002 | Walsh et al. | |
| 2003/0004554 A1 | 1/2003 | Riff et al. | |
| 2003/0050542 A1 | 3/2003 | Reihl et al. | |
| 2003/0088682 A1 | 5/2003 | Hlasny | |
| 2003/0099682 A1 | 5/2003 | Moussy et al. | |
| 2003/0153026 A1 | 8/2003 | Alarcon et al. | |
| 2003/0171666 A1 | 9/2003 | Loeb et al. | |
| 2003/0208166 A1 | 11/2003 | Schwartz | |
| 2004/0106215 A1 | 6/2004 | Lehmann | |
| 2004/0106951 A1 | 6/2004 | Edman et al. | |
| 2004/0143221 A1 | 7/2004 | Shadduck | |
| 2004/0161853 A1 | 8/2004 | Yang et al. | |
| 2004/0176669 A1 | 9/2004 | Colvin, Jr. | |
| 2004/0195528 A1 | 10/2004 | Reece et al. | |
| 2004/0234962 A1 | 11/2004 | Alarcon et al. | |
| 2004/0258732 A1 | 12/2004 | Shikinami | |
| 2004/0259270 A1 | 12/2004 | Wolf | |
| 2005/0027175 A1 | 2/2005 | Yang | |
| 2005/0043606 A1 | 2/2005 | Pewzner et al. | |
| 2005/0095174 A1 | 5/2005 | Wolf | |
| 2005/0096587 A1 | 5/2005 | Santini, Jr. et al. | |
| 2005/0118726 A1 | 6/2005 | Schultz et al. | |
| 2005/0119737 A1 | 6/2005 | Bene et al. | |
| 2005/0154374 A1 | 7/2005 | Hunter et al. | |
| 2005/0182389 A1 | 8/2005 | LaPorte et al. | |
| 2005/0237518 A1 | 10/2005 | Colvin, Jr. et al. | |
| 2005/0245799 A1 | 11/2005 | Brauker et al. | |
| 2006/0002890 A1 | 1/2006 | Hersel et al. | |

(56) References Cited

U.S. PATENT DOCUMENTS

| | | |
|---|---|---|
| 2006/0002969 A1 | 1/2006 | Kyriakides et al. |
| 2006/0089548 A1 | 4/2006 | Hogan |
| 2006/0148983 A1 | 7/2006 | Muller et al. |
| 2006/0155179 A1 | 7/2006 | Muller et al. |
| 2006/0252976 A1 | 11/2006 | Rosero |
| 2006/0270919 A1 | 11/2006 | Brenner |
| 2006/0275340 A1 | 12/2006 | Udipi et al. |
| 2006/0289307 A1 | 12/2006 | Yu et al. |
| 2007/0002470 A1 | 1/2007 | Domschke et al. |
| 2007/0004046 A1 | 1/2007 | Abbott |
| 2007/0010702 A1 | 1/2007 | Wang et al. |
| 2007/0030443 A1 | 2/2007 | Chapoy et al. |
| 2007/0093617 A1 | 4/2007 | DesNoyer et al. |
| 2007/0105176 A1 | 5/2007 | Ibey et al. |
| 2007/0134290 A1 | 6/2007 | Rowland et al. |
| 2007/0135698 A1 | 6/2007 | Shah et al. |
| 2007/0244379 A1 | 10/2007 | Boock et al. |
| 2007/0270675 A1 | 11/2007 | Kane et al. |
| 2008/0020012 A1 | 1/2008 | Ju et al. |
| 2008/0075752 A1 | 3/2008 | Ratner et al. |
| 2008/0136052 A1 | 6/2008 | Pelrine et al. |
| 2008/0139903 A1 | 6/2008 | Bruce et al. |
| 2008/0191585 A1 | 8/2008 | Pelrine et al. |
| 2008/0249381 A1 | 10/2008 | Muller et al. |
| 2009/0005663 A1 | 1/2009 | Parker et al. |
| 2009/0131773 A1 | 5/2009 | Struve et al. |
| 2009/0187084 A1 | 7/2009 | Kristensen et al. |
| 2009/0221891 A1 | 9/2009 | Yu et al. |
| 2009/0270953 A1 | 10/2009 | Ecker et al. |
| 2010/0081906 A1 | 4/2010 | Hayter et al. |
| 2010/0113901 A1 | 5/2010 | Zhang et al. |
| 2010/0123121 A1 | 5/2010 | Taylor |
| 2010/0160749 A1 | 6/2010 | Gross et al. |
| 2010/0185066 A1 | 7/2010 | March |
| 2010/0202966 A1 | 8/2010 | Gross et al. |
| 2010/0222657 A1 | 9/2010 | Ibey et al. |
| 2010/0240975 A1 | 9/2010 | Goode, Jr. et al. |
| 2010/0249548 A1 | 9/2010 | Mueller |
| 2010/0303772 A1 | 12/2010 | McMillan et al. |
| 2010/0305413 A1 | 12/2010 | Paterson |
| 2010/0324383 A1 | 12/2010 | Epstein et al. |
| 2011/0028806 A1 | 2/2011 | Merritt et al. |
| 2011/0036994 A1 | 2/2011 | Frayling |
| 2011/0154641 A1 | 6/2011 | Pelrine et al. |
| 2011/0155307 A1 | 6/2011 | Pelrine et al. |
| 2011/0224514 A1 | 9/2011 | Muller et al. |
| 2011/0230835 A1 | 9/2011 | Muller et al. |
| 2011/0306511 A1 | 12/2011 | Lea |
| 2012/0123276 A1 | 5/2012 | Govari et al. |
| 2012/0140094 A1 | 6/2012 | Shpunt et al. |
| 2012/0172692 A1 | 7/2012 | Tamada et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0245445 A1 | 9/2012 | Black et al. |
| 2012/0258551 A1 | 10/2012 | Herbrechtsmeier et al. |
| 2012/0265034 A1 | 10/2012 | Wisniewski et al. |
| 2012/0283538 A1 | 11/2012 | Rose et al. |
| 2012/0296311 A1 | 11/2012 | Brauker et al. |
| 2013/0006069 A1 | 1/2013 | Gil et al. |
| 2013/0022648 A1 | 1/2013 | Maginness et al. |
| 2013/0030273 A1 | 1/2013 | Tapsak et al. |
| 2013/0060105 A1 | 3/2013 | Shah et al. |
| 2013/0158413 A1 | 6/2013 | Lisogurski et al. |
| 2013/0172699 A1 | 7/2013 | Rebec et al. |
| 2013/0211212 A1 | 8/2013 | Stumber |
| 2013/0211213 A1 | 8/2013 | Dehennis et al. |
| 2013/0213110 A1 | 8/2013 | Papadimitrakopoulos et al. |
| 2013/0229660 A1 | 9/2013 | Goldschmidt et al. |
| 2013/0231542 A1 | 9/2013 | Simpson et al. |
| 2013/0302908 A1 | 11/2013 | Amiss et al. |
| 2013/0310666 A1 | 11/2013 | Shults et al. |
| 2013/0310670 A1 | 11/2013 | Boock et al. |
| 2013/0311103 A1 | 11/2013 | Cooper et al. |
| 2013/0313130 A1 | 11/2013 | Little et al. |
| 2013/0337468 A1 | 12/2013 | Muller et al. |
| 2014/0000338 A1 | 1/2014 | Luo et al. |
| 2014/0148596 A1 | 5/2014 | Dichtel et al. |
| 2014/0275869 A1 | 9/2014 | Kintz et al. |
| 2014/0357964 A1 | 12/2014 | Wisniewski et al. |
| 2014/0364707 A1 | 12/2014 | Kintz et al. |
| 2016/0213288 A1 | 7/2016 | Wisniewski et al. |
| 2016/0374556 A1 | 12/2016 | Colvin et al. |
| 2017/0087376 A1 | 3/2017 | McMillan et al. |
| 2017/0325722 A1 | 11/2017 | Wisniewski et al. |
| 2020/0008716 A1 | 1/2020 | Kintz et al. |

FOREIGN PATENT DOCUMENTS

| | | |
|---|---|---|
| CN | 101087630 A | 12/2007 |
| EP | 1937136 B1 | 7/2008 |
| EP | 2517619 B1 | 5/2013 |
| JP | 2004-537344 | 12/2004 |
| JP | 2007-044512 A | 2/2007 |
| JP | 2008-541881 | 11/2008 |
| WO | WO 98/06406 | 2/1998 |
| WO | WO 2000/002048 | 1/2000 |
| WO | WO 2001/006579 | 1/2001 |
| WO | WO 2001/018543 | 3/2001 |
| WO | WO 2002/087610 | 11/2002 |
| WO | WO 2005/059037 | 6/2005 |
| WO | WO 2005/120631 | 12/2005 |
| WO | WO 2006/004595 | 1/2006 |
| WO | WO 2006/044972 | 4/2006 |
| WO | WO 2006/065266 | 6/2006 |
| WO | WO 2006/130461 | 12/2006 |
| WO | WO 2007/065653 | 6/2007 |
| WO | WO 2007/126444 | 11/2007 |
| WO | WO 2008/105791 | 9/2008 |
| WO | WO 2008/141241 | 11/2008 |
| WO | WO 2008/143651 | 11/2008 |
| WO | WO 2009/019470 | 2/2009 |
| WO | WO 2009/087373 | 7/2009 |
| WO | WO 2009/106805 | 9/2009 |
| WO | WO 2010/116142 | 10/2010 |
| WO | WO 2010/133831 | 11/2010 |
| WO | WO 2011/101624 | 8/2011 |
| WO | WO 2011/101625 | 8/2011 |
| WO | WO 2011/101626 | 8/2011 |
| WO | WO 2011/101627 | 8/2011 |
| WO | WO 2011/101628 | 8/2011 |
| WO | WO 2013/132400 | 9/2013 |

OTHER PUBLICATIONS

Alexeev et al., "High ionic strength glucose-sensing photonic crystal," Anal. Chem., 75:2316-2323 (2003).

Alexeev et al., "Photonic crystal glucose-sensing material for non-invasive monitoring of glucose in tear fluid," Clinical Chemistry, 50(12):2353-2360 (2004).

Aslan et al., "Nanogold plasmon-resonance-based glucose sensing 2: wavelengthratiometric resonance light scattering," Anal. Chem., 77(7):2007-2014 (2005).

Badylak et al., "Immune response to biologic scaffold materials," Seminars in Immunology, 20(2):109-116 (2008).

Ballerstadt et al., "Competitive-binding assay method based on fluorescence quenching of ligands held in close proximity by a multivalent receptor," Anal. Chem., Acta. 345:203-212 (1997).

Bhardwaj, U. et al., "A review of the development of a vehicle for localized and controlled drug delivery for implantable biosensors," Journal of Diabetes Science and Technology, 2(6):1016-1029 (2008).

Billingsley et al., "Fluorescent nano-optodes for glucose detection," Anal. Chem., 82(9):3707-3713 (2010).

Brasuel et al., "Fluorescent nanosensors for intracellular chemical analysis: decyl methacrylate liquid polymer matrix and ion-exchange-based potassium pebble sensors with real-time application to viable rat C6 glioma cells," Anal. Chem., 73(10):2221-2228 (2001).

(56) References Cited

OTHER PUBLICATIONS

Brasuel et al., "Liquid polymer nano-pebbles for CL-analysis and biological applications," Analyst, 128(10):1262-1267 (2003).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Cordeiro, P.G. et al., "The protective effect of L-arginine on ischemia-reperfusion injury in rat skin flaps," Plast Reconstruct Surg., 100(5):1227-1233 (1997).
Dunphy, I. et al., "Oxyphor R2 and G2: phosphors for measuring oxygen by oxygen-dependent quenching phosphorescence," Anal. Biochem., 310:191-198 (2002).
Garg, S. K. et al., "Improved glucose excursions using an implantable real-time continuous glucose sensor in adults with Type 1 diabetes," Diabetes Care, 27(3):734-738 (2004).
Henninger, N., et al., "Tissue response to subcutaneous implantation of glucose-oxidase-based glucose sensors in rats," Biosens Bioelectron, 23(1):26-34 (2007).
Horgan et al., "Crosslinking of phenylboronic acid receptors as a means of glucose selective holographic detection," Biosensors and Bioelectronics, 21(9):1838-1845 (2006).
Ibey et al., "Competitive binding assay for glucose based on glycodendrimer fluorophore conjugates," Anal. Chem., 77(21):7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009.
Klimowicz, A. et al., "Evaluation of skin penetration of topically applied drugs by cutaneous microdialysis:acydovir vs salicylic acid," J Clin Pharm Ther, 3(2):143-148 (2007).
Kloxin, A. M. et al., "Photodegradable hydrogels for dynamic tuning of physical and chemical properties," Science, 324:59-63 (2009).
Leavesley, S. J. et al., "Hyperspectral imaging microscopy for identification and quantitative analysis of fluorescently-labeled cells in highly autofluorescent tissue," J. Biophontonics, Jan. 2012;5(1):67-84. doi: 10.1002/jbio.201100066. Epub Oct. 11, 2011.
Mansouri et al., "A miniature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nagler, A. et al., "Topical treatment of cutaneous chronic graft versus host disease with halofuginone: a novel inhibitor of collagen Type 1 synthesis," Transplantation, 68(11):1806-1809 (1999).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Onuki, Y. et al., "A review of the biocompatibility of implantable devices: Current challenges to overcome foreign body response," Journal of Diabetes Science and Technology, 2(6):1003-1015 (2008).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Pickup, J. C. et al., "In vivo glucose monitoring: the clinical reality and the promise," Biosens Bioelectron., 20(10):1897-1902 (2005), Available online Oct. 3, 2004.
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer micro-fibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Schultz et al., "Affinity sensor: a new technique for developing implantable sensors for glucose and other metabolites," Diabetes Care, 5(3)245-253 (1982).
Shibata, H. et al., "Injectable hydrogel microbeads for fluorescence-based in vivo continuous glucose monitoring", Proceedings of the National Academy of Sciences of the United States of America, Oct. 19, 2010, vol. 107, No. 42, pp. 17894-17898.
Smith, J. L., "The Pursuit of Noninvasive Glucose: 'Hunting the Deceitful Turkey,'" (2006).
Srivastava et al., "Application of self-assembled ultrathin film coatings to stabilize macromolecule encapsulation in alginate microspheres," J of Microencapsulation, 22(4):397-411 (2005).
Srivastava et al., "Stabilization of glucose oxidase in alginate microspheres with photo reactive diazoresin nanofilm coatings," Biotechnology and Bioengineering, 91(1):124-131 (2005).
Takano et al., "An oxo-bacteriochlorin derivative for long-wavelength fluorescence ratiometric alcohol sensing," Analyst, 135:2334-2339 (2010).
Tian et al., "Dually fluorescent sensing of PH and dissolved oxygen using a membrane made from polymerizable sensing monomers," Sensors and Actuators B, 147:714-722 (2010).
Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).
Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chemistry Materials, 22(6):2069-2078 (2010).

(56) References Cited

OTHER PUBLICATIONS

Vidavalur, R. et al., "Sildenafil induces angiogenic response in human coronary arterioloar endothelial cells through the expression of thioredoxin, hemaoxygenase, and VEGF," Vasc Pharm, 45(2):91-95 (2006).

Ward, W. K. et.al., "The effect of microgeometry, implant thickness and polyurethane chemistry on the foreign body response to subcutaneous implants," Biomaterials, 23(21):4185-4192 (2002).

Wisniewski, N. et.al., "Characterization of implantable biosensor membrane fouling," Fresen J Anal Chem., 366 (6-7):611-621 (2000).

Wisniewski, N. et al., "Methods for reducing biosensor membrane biofouling," Colloids and Surfaces B: Biointerfaces, 18:197-219 (2000).

Woderer, S., "Continuous glucose monitoring in interstitial fluid using glucose oxidase-based sensor compared to established blood glucose measurement in rats," Anal Chim Acta., 581(1):7-12 (2007), Available online Aug. 18, 2006.

Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.

Single-channel sensor 110

Detail A

SYSTEM AND SINGLE-CHANNEL BIOSENSOR FOR AND METHOD OF DETERMINING ANALYTE VALUE

CROSS REFERENCE TO RELATED APPLICATIONS

This application is a non-provisional of and claims priority to U.S. Patent Application No. 62/438,113, filed Dec. 22, 2016, and entitled "System and Single-Channel Biosensor for and Methods of Determining Analyte Value," which is hereby incorporated by reference in its entirety.

TECHNICAL FIELD

The presently disclosed subject matter relates generally to sensors for monitoring analyte levels in the body and more particularly to a system and single-channel luminescent sensor for and method of determining analyte value.

BACKGROUND

For the management of many conditions, the regular measurement of analytes in vivo is desirable. It has been a long-standing objective of both medical science and the military to implant sensors inside the human body that continuously and accurately determine a quantity, concentration and/or changes in physiologic, metabolic, or fatigue status; measure the concentration of biothreat or therapeutic agents in vivo; and/or provide early detection of disease prior to the onset of symptoms. It has long been desired that such sensors and/or measurements be non-invasive and involve minimal user maintenance. Furthermore, it is desirable to achieve sensor longevity of months to years in actual user environments.

For example, it is known that blood glucose measurements can be used to determine insulin dose amounts for diabetic patients. Furthermore, it has been demonstrated that in the long term care of the diabetic patient better control of the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, biosensors exist that can be implanted in tissue. For example, biosensors, such as those shown and described in U.S. Patent Application Publication No. 2012/0265034 and U.S. Pat. No. 9,375,494, the disclosures of which are hereby incorporated by reference in their entirety, can be implanted a few millimeters under the skin. The intensity of a certain luminescent dye can modulate based on the amount of analyte present, wherein the intensity of the emission light can be correlated to the analyte concentration. However, intensity-based systems can be challenging because the detector (or reader) is subject to potential sources of error and noise that make it difficult to get an accurate analyte measurement. For example, when relying on intensity-based measurements, there are accuracy can be negatively affected by dynamic tissue optics between the implanted sensor and the surface of the skin, where the reader is located, varying. A need therefore exists for single-channel luminescent sensors.

SUMMARY

Some embodiments described herein relate to a sensor that includes an analyte-sensing dye and a reference dye. The analyte-sensing dye and the reference dye can each be configured to be excited by a common illumination signal. Similarly stated, the excitation spectrum of the analyte-sensing dye and the reference dye can be the same, substantially the same, and/or overlapping. The analyte-sensing dye can be configured to emit an analyte-dependent optical signal in the presence of an analyte. Similarly stated, the intensity and/or duration of the analyte-dependent optical signal can be modulated by a quantity and/or concentration of the analyte in the environment of the sensor. The reference dye can be configured to emit an analyte-independent optical signal. Similarly stated, the intensity and/or duration of the analyte-independent optical signal is not influenced by the quantity and/or concentration of the analyte. The analyte-dependent optical signal and the analyte-independent optical signal have an analyte-dependent spectrum and an analyte-independent spectrum, respectfully. The analyte-dependent optical spectrum and the analyte-independent spectrum can be the same, substantially the same, and/or overlapping. The analyte-dependent optical signal can have a duration of lifetime that is shorter than a duration or lifetime of the analyte-independent optical signal.

BRIEF DESCRIPTION OF THE DRAWINGS

Reference will now be made to the accompanying Drawings, which are not necessarily drawn to scale, and wherein.

DETAILED DESCRIPTION

Figure 1:
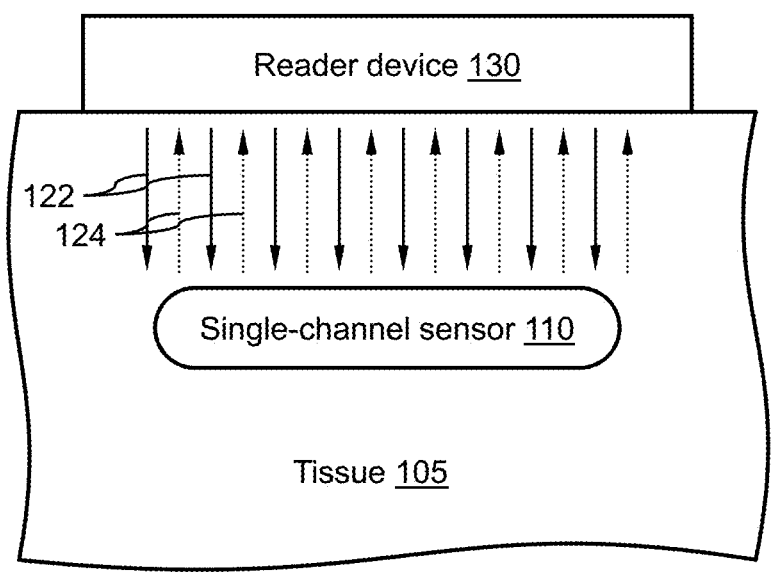
FIG. 1 illustrates a block diagram of an analyte detection system for determining an analyte value using an implantable single-channel sensor and a detector device, according to an embodiment.

The presently disclosed subject matter now will be described more fully hereinafter with reference to the accompanying Drawings. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a system and single-channel luminescent sensor and method of determining analyte value (e.g., analyte concentration). Namely, an analyte detection system is described that includes a single-channel luminescent sensor that, in some embodiments, may be implanted in tissue (e.g., a few millimeters under the skin) in combination with a reader device that may be on the surface of the skin. Further, the analyte detection system includes processing capability for processing any information from the reader device. As used herein, luminescence is the emission of light as a result of the excitation of atoms by energy other than heat and includes, without limitation, chemiluminescence and fluorescence.

According to some embodiments described herein, a single-channel luminescent sensor of can include some or all of the following:
(1) a short-lifetime (e.g., about ≤50 ns) analyte-sensing dye wherein the emission intensity modulates with the amount of analyte present;
(2) a long-lifetime (e.g., about ≥1 µs) reference dye that is a non-analyte-sensing dye wherein the emission intensity does not modulate based on an analyte;
(3) the absorption spectrums of the short-lifetime analyte-sensing dye and the long-lifetime reference are substantially the same or at least overlapping;
(4) the short-lifetime analyte-sensing dye and the long-lifetime reference dye wherein the emission spectrums are substantially the same or at least overlapping; and/or
(5) the short-lifetime analyte-sensing dye and the long-lifetime reference dye that are distinguishable optically by their different emission lifetime characteristics (e.g., about ≤50 ns lifetime emission vs. about ≥1 µs lifetime emission).

According to some embodiments described herein, a reader device can include some or all of the following:
(1) a single light source and/or multiple light sources that have substantially the same illumination spectrum. Namely, because the absorption spectrums of the short-lifetime analyte-sensing dye and the long-lifetime reference dye are substantially the same or at least overlapping, only one light source and/or illumination spectrum is needed for illuminating and exciting both the short-lifetime analyte-sensing dye and the long-lifetime reference dye simultaneously. By contrast, if the absorption spectrums of the short-lifetime analyte-sensing dye and the long-lifetime reference dye were not substantially the same or at least overlapping, then two light sources and/or two illumination steps would be required. Therefore, according to some embodiments described herein, a reader device of an analyte detection system avoids the requirement of a second light source, second illumination spectrum, and/or a second illumination step; and
(2) a single detector device and/or multiple detectors operable to detect substantially the same detection spectrum. Namely, because the emission spectrums of the short-lifetime analyte-sensing dye and the long-lifetime reference dye are substantially the same or at least overlapping, only one detector device, detection spectrum, emission filter, and/or output spectrum from one or more emission filters is needed for detecting the optical signals from both the short-lifetime analyte-sensing dye and the long-lifetime reference dye simultaneously. By contrast, if the emission spectrums of the short-lifetime analyte-sensing dye and the long-lifetime reference dye were not substantially the same or were not at least overlapping, then two detector devices, detection spectrums, and/or two detection steps would be required. Therefore, according to some embodiments described herein a reader device of an analyte detection system avoids the requirement of a second detector device, detection spectrum, and/or a second detection step.

Some embodiments described herein relate to a sensor that includes an analyte-sensing dye and a reference dye. The analyte-sensing dye and the reference dye can each be configured to be excited by a common illumination signal. Similarly stated, the excitation spectrum of the analyte-sensing dye and the reference dye can be the same, substantially the same, and/or overlapping. The analyte-sensing dye can be configured to emit an analyte-dependent optical signal in the presence of an analyte. Similarly stated, the intensity and/or duration of the analyte-dependent optical signal can be modulated by a quantity and/or concentration of the analyte in the environment of the sensor. The reference dye can be configured to emit an analyte-independent optical signal. Similarly stated, the intensity and/or duration of the analyte-independent optical signal is not influenced by the quantity and/or concentration of the analyte. The analyte-dependent optical signal and the analyte-independent optical signal have an analyte-dependent spectrum and an analyte-independent spectrum, respectfully. The analyte-dependent optical spectrum and the analyte-independent spectrum can be the same, substantially the same, and/or overlapping. The analyte-dependent optical signal can have a duration of lifetime that is shorter than a duration or lifetime of the analyte-independent optical signal.

Some embodiments described herein relate to a reader configured to excite the sensor described immediately above and/or detect optical signals emitted from the sensor. The reader can include a light source configured to emit an illumination signal that is configured to excite both the analyte-dependent optical signal and the analyte-independent optical signal. Similarly stated, illumination signal can have a component within the excitation spectrum of both the analyte-sensing dye and the reference dye. The reader can include a detector configured to detect the analyte-dependent optical signal and the analyte-independent signal that are emitted from the sensor.

Some embodiments described herein relate to a method that includes illuminating a sensor with an illumination signal. An analyte-dependent optical signal and an analyte-independent optical signal emitted from the sensor can be detected. A spectrum of the analyte-dependent optical signal can be the same as, substantially the same as, and/or overlapping a spectrum of the analyte-independent optical signal. A quantity of an analyte can be determined based on a ratio of an intensity of the analyte-dependent optical signal and an intensity of the analyte-independent optical signal.

The fluorescence lifetime is a measure of the time a fluorophore spends in the excited state before returning to the ground state by emitting a photon. The lifetimes of fluorophores can range from, for example, a few picoseconds to hundreds of microseconds. As described herein, the lifetime of a fluorophore is the duration of time for the fluorophore to reach 37% of the maximum (initial) intensity after the excitation signal has been removed.

Further, a method is provided of using the presently disclosed analyte detection system to determine an analyte value (or analyte concentration), according to an embodiment. Namely, in the method, even though the short-lifetime analyte-sensing dye and the long-lifetime reference dye in the single-channel luminescent sensor have substantially the same or at least overlapping emission spectrums, the short-lifetime analyte-sensing dye and the long-lifetime reference dye are distinguishable optically by their different lifetime characteristics (e.g., about ≤50 ns lifetime vs. about ≥1 μs lifetime). Namely, the optical signal captured by a detector device has both a short-lifetime component from the short-lifetime analyte-sensing dye and a long-lifetime component from the long-lifetime reference dye. Accordingly, in the presently disclosed analyte detection system, information can be captured from and/or about two different dyes using a single color (spectrum) channel by looking at short-lifetime intensity vs. long-lifetime intensity of emitted and/or detected light.

Further, the method can use a ratio of the short-lifetime intensity (SLI) of the short-lifetime analyte-sensing dye to the long-lifetime intensity (LLI) of the long-lifetime reference dye. This ratio is hereafter called the intensity ratio, which is SLI/LLI. In the method, the intensity ratio can be used to normalize the analyte value for dynamic and tissue optics variations that occur in the tissue between the single-channel luminescent sensor and the surface of the skin where the reader device is located. In so doing, the presently disclosed analyte detection system and method provide a highly quantitative analyte measurement wherein the sensitivity to variables other than the analyte is reduced or substantially eliminated as compared with conventional sensing methods. Namely, as compared with conventional sensing methods, the analyte detection system and method provide an analyte measurement that has little or no sensitivity to, for example, motion artifacts (e.g., reader position), tissue artifacts (e.g., depth, pressure), oxygen artifacts (e.g., tissue oxygenation), temperature artifacts, and the like in order to make the analyte measurement more accurate.

Conventional sensing methods typically use a short-lifetime analyte-sensitive dye and a short-lifetime reference dye that have different emission spectrums (colors). Consequently, two different light sources (illumination spectrums) and two different detectors (detection spectrums) are typically required. However, tissue absorbs and/or scatters light of different wavelengths differently, which can present problems for conventional sensing methods. Consequently, corrections based on the reference signal of conventional sensing methods can be subject to errors because the reference signal has a different spectrum than the analyte-sensitive dye. By contrast, an advantage of the presently disclosed analyte detection system and method is that because the short-lifetime analyte-sensing dye and the long-lifetime reference dye are in the same or at least overlapping spectrums, more accurate measurements and/or corrections are possible as compared with an analyte-sensitive dye and a reference dye that do not have the same or overlapping spectrums.

FIG. 1 is a block diagram of an example of the presently disclosed analyte detection system 100 for determining an analyte value using an implantable single-channel luminescent sensor and a detector device, according to an embodiment. For example, analyte detection system 100 includes a single-channel sensor 110 implanted in tissue 105. For example, single-channel sensor 110 may be implanted a few millimeters (e.g., 1-10 mm) under the skin of the user. Analyte detection system 100 also includes a reader device 130. Reader device 130 may be provided as a patch that can be placed on the surface of the skin (i.e., tissue 105) in close proximity to (e.g., over) single-channel sensor 110. Reader device 130 is configured to communicate with (send signals to and/or receive signals from) the single-channel sensor through the skin and/or tissue. Similarly stated, reader device 130 is not physically coupled to the single-channel sensor 110.

When implanted in tissue 105, single-channel sensor 110 is in good contact (close proximity) to capillaries and has direct access to measurements of blood and/or interstitial fluid. Single-channel sensor 110 includes the short-lifetime analyte-sensing dye and the long-lifetime reference dye. The short-lifetime analyte-sensing dye in single-channel sensor 110 is an analyte-specific dye sensitive to the analyte of interest (e.g., oxygen, glucose, lactate, carbon dioxide ($CO_2$), $H^+$, $OH^-$, etc.). Similarly stated, an intensity of light emitted by the short-lifetime analyte-sensing dye can be indicative a quantity and/or concentration of the analyte of interest. In one example, short-lifetime analyte-sensing dye is a short-lifetime glucose-sensing dye. In this example, single-channel sensor 110 is a glucose sensor.

In single-channel sensor 110, the absorption spectrums of the short-lifetime analyte-sensing dye and the long-lifetime reference dye are substantially the same or at least overlapping. In single-channel sensor 110, the emission spectrums of the short-lifetime analyte-sensing dye and the long-lifetime reference dye are substantially the same or at least overlapping. Accordingly, single-channel sensor 110 is capable of emitting, in response to excitation light, at least one analyte-dependent optical signal (from the short-lifetime analyte-sensing dye) and at least one analyte-independent optical signal (from the long-lifetime reference dye), wherein the analyte-dependent optical signal and the analyte-independent optical signal may be distinguishable by their different lifetime characteristics (e.g., about ≤50 ns vs. about ≥1 μs). More details of an example of single-channel sensor 110 are shown and described hereinbelow with reference to FIG. 2.

Reader device 130 includes a light source (not shown) for illuminating the short-lifetime analyte-sensing dye and the long-lifetime reference dye, an optical detector device (not shown) for collecting the emission light from the short-lifetime analyte-sensing dye and the long-lifetime reference dye, and various other optical components, such as optical filters (not shown). For example, the light source of reader device 130 emits excitation light 122 toward single-channel sensor 110. The optical detector device of reader device 130 collects emission light 124 from single-channel sensor 110. More details of examples of reader device 130 are shown and described hereinbelow with reference to FIG. 3 and FIG. 4.

Figure 2:
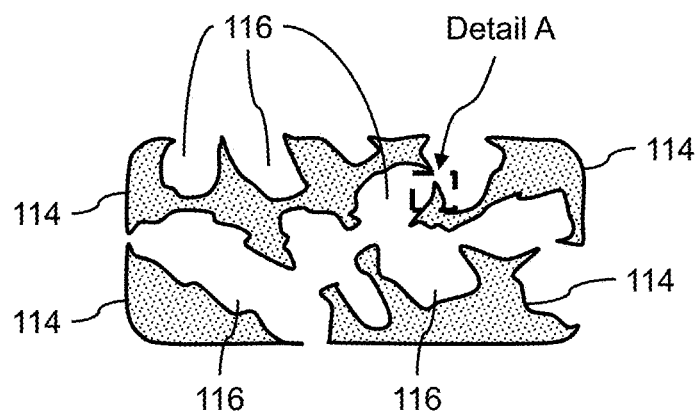
FIG. 2 illustrates a side view and a detail view of an embodiment of an implantable single-channel sensor.
Figure 2:
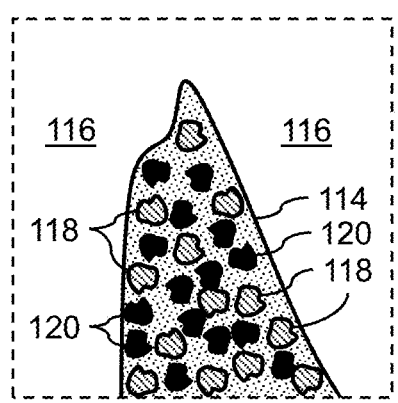

FIG. 2 is a side view and a detail view of an embodiment of the implantable single-channel sensor 110 of the presently disclosed analyte detection system 100. In one example, single-channel sensor 110 may be a porous or non-porous implantable sensor. In an embodiment, the sensor may be tissue-integrating. In another embodiment, the sensor may not be tissue-integrating. The single-channel sensor 110 may include structural and/or functional features of tissue-integrating sensors described in U.S. Patent Publication. No. 2012/0265034, entitled "Tissue-integrating sensors," filed on Oct. 6, 2011 ("the '034 patent publication"); the entire disclosure of which is incorporated herein by reference. The '034 patent publication describes tissue-integrating sensors, systems including these sensors and methods of using these sensors and systems for the detection of one or more analytes.

As shown, single-channel sensor 110 includes a tissue-integrating scaffold 114 that defines a plurality of pores 116 within single-channel sensor 110. Further, all, some, or groups of pores 116 may be interconnected. Tissue-integrating scaffold 114 can be, for example, a hydrogel based structure that includes one or more types of analyte sensing particles and/or reference particles mixed or embedded therein. "Hydrogel" means a material that absorbs a solvent (e.g. water), undergoes rapid swelling without discernible dissolution, and maintains three-dimensional networks capable of reversible deformation.

In one example, two different types of sensing moieties (e.g., sensing moieties 118 and reference moieties 120) can be embedded in the tissue-integrating scaffold 114, as shown in Detail A of FIG. 2. In another example, the tissue-integrating scaffold 114 may be made up solely or primarily of the two different types of sensing moieties (e.g., sensing moieties 118 and reference moieties 120). For example, sensing particles can be bonded together using any suitable method (chemical, adhesive, thermal, etc.). In some examples, the sensing particles include a polymer, such as PEG-coated particles (e.g., microspheres). In other examples, tissue-integrating scaffold 114 includes a polymer that itself is composed of sensing moieties 118 and reference moieties 120.

The tissue-integrating scaffold 114 provides good contact (close proximity) to capillaries and have direct access to measurements of interstitial fluid. The single-channel sensor 110 constructed to promote tissue-integration and/or vascularization. Accordingly, tissue-integrating scaffold 114 and pores 116 collectively encourage capillary growth into pores 116 and into or nearby the sensing media (e.g., sensing moieties 118 and reference moieties 120).

In one example, sensing moieties 118 of single-channel sensor 110 may be a first type of luminescent dye (e.g., fluorescent dye), which is the short-lifetime analyte-sensing dye having a certain absorption spectrum and a certain emission spectrum. The sensing moieties 118 are hereafter called the analyte sensing moieties 118. With respect to analyte sensing moieties 118, the luminescence emission intensity varies in dependence upon the amount, concentration and/or presence of target analyte in the body of the individual (e.g., in tissue 105).

Examples of analytes that may be detected using analyte sensing moieties 118 of single-channel sensor 110 include, but are not limited to, oxygen, reactive oxygen species, glucose, lactate, pyruvate, cortisol, creatinine, urea, sodium, magnesium, calcium, potassium, vasopressin, hormones (e.g., Luteinizing hormone), $H^+$, $OH^-$, $CO_2$, cytokines, chemokines, eicosanoids, insulin, leptins, small molecule drugs, ethanol, myoglobin, nucleic acids (RNAs, DNAs) fragments, polypeptides, single amino acids, and the like.

Further, reference moieties 120 of single-channel sensor 110 may be a second type of luminescent dye (e.g., fluorescent dye), which is the long-lifetime reference dye having substantially the same or at least overlapping absorption spectrum and emission spectrum as the analyte sensing moieties 118. With respect reference moieties 120, the luminescence emission intensity does not vary in dependence upon the amount or presence of target analyte or other chemicals in the environment containing the reference moiety. However, in single-channel sensor 110, analyte sensing moieties 118 and reference moieties 120 may be distinguishable optically by their different lifetime characteristics (e.g., about ≤50 ns lifetime vs. about ≥1 μs lifetime).

In one example, analyte sensing moieties 118 may be moieties that include a short-lifetime fluorescent dye, such as rosamine that has a fluorescence lifetime of from about 0.1 ns to about 500 ns or from about 0.5 ns to about 50 ns or from about 1 ns to about 5 ns; an absorption wavelength of from about 600 nm to about 950 nm or from about 600 nm to about 800 nm or from about 650 nm to about 750 nm; and an emission wavelength of from about 620 nm to about 1000 nm or from about 600 nm to about 800 nm or from about 650 nm to about 750 nm. Examples of other short-lifetime fluorescent dyes include, but are not limited to, cyanine, hemicyanine, fluorone, oxazine, phenanthridine, rhodamine, rosamine, indolium, quinolinium, benzophenoxazine, benzopyrillium, bisindoylmaleimide, boron-dipyrromethene, boron-aza-dipyrromethene, carbopyronins, perylene, benzoxanthenium, xanthene, fluorescein, squaraine, coumarin, anthracene, tetracene, pentacene, and pyrene dye.

The corresponding reference moieties 120 may be moieties that include a long-lifetime fluorescent dye, such as chromium(III)-doped yttrium aluminum borate (Cr-YAB) that has a fluorescence lifetime of from about 1 μs to about 100 ms or from about 10 μs to about 1 ms or from about 10 μs to about 500 μs or from about 20 μs to about 300 μs; an absorption wavelength of from about 600 nm to about 950 nm or from about 600 nm to about 800 nm or from about 650 nm to about 700 nm; and an emission wavelength of from about 620 nm to about 1000 nm or from about 600 nm to about 800 nm or from about 650 nm to about 700 nm. Examples of other long-lifetime fluorescent dyes include, but are not limited to, metalloporphyrin, transition-metal ligand complex, rare earth ligand complex, transition-metal doped or rare earth doped oxide or nitride or silicate.

Although single channel sensor 110 is shown with a single type of analyte sensing moiety 118 and a single type of reference moiety 120, in other embodiments, sensors can include any number of types of sensing moieties or reference moieties. For example, a sensor can include two or more types of sensing moieties, and each sensing moiety can be configured to emit an optical signal that is dependent on a different analyte. Each type of sensing moiety can be paired with a type of reference moiety, or a single reference moiety can serve as a reference to multiple types of sensing moieties. In some embodiments, each type of sensing moiety and/or each type of reference moiety can be configured to be excited by a single excitation spectrum and/or emit at a single emission spectrum (or overlapping emission spectrums). In other embodiments, each sensing moiety/reference moiety pair can be excited by a single excitation spectrum and/or emit at a single emission spectrum (or overlapping emission spectrums), but the excitation spectrum and/or emission spectrum for different pairs of sensing moieties and reference moieties can be different.

Further, in some embodiments, it can be beneficial if the concentrations and/or quantum efficiencies of the selected short-lifetime analyte-sensing dye and long-lifetime reference dye are comparable so that they both may emit at about the same intensity. Exemplary analyte sensing moieties 118 are described in U.S. Patent App. Nos. 62/439,363 and/or 62/439,364, each entitled "Near-IR Glucose Sensors," each filed on Dec. 27, 2016, and the entire disclosure of each of which is incorporated herein by reference.

Figure 3:
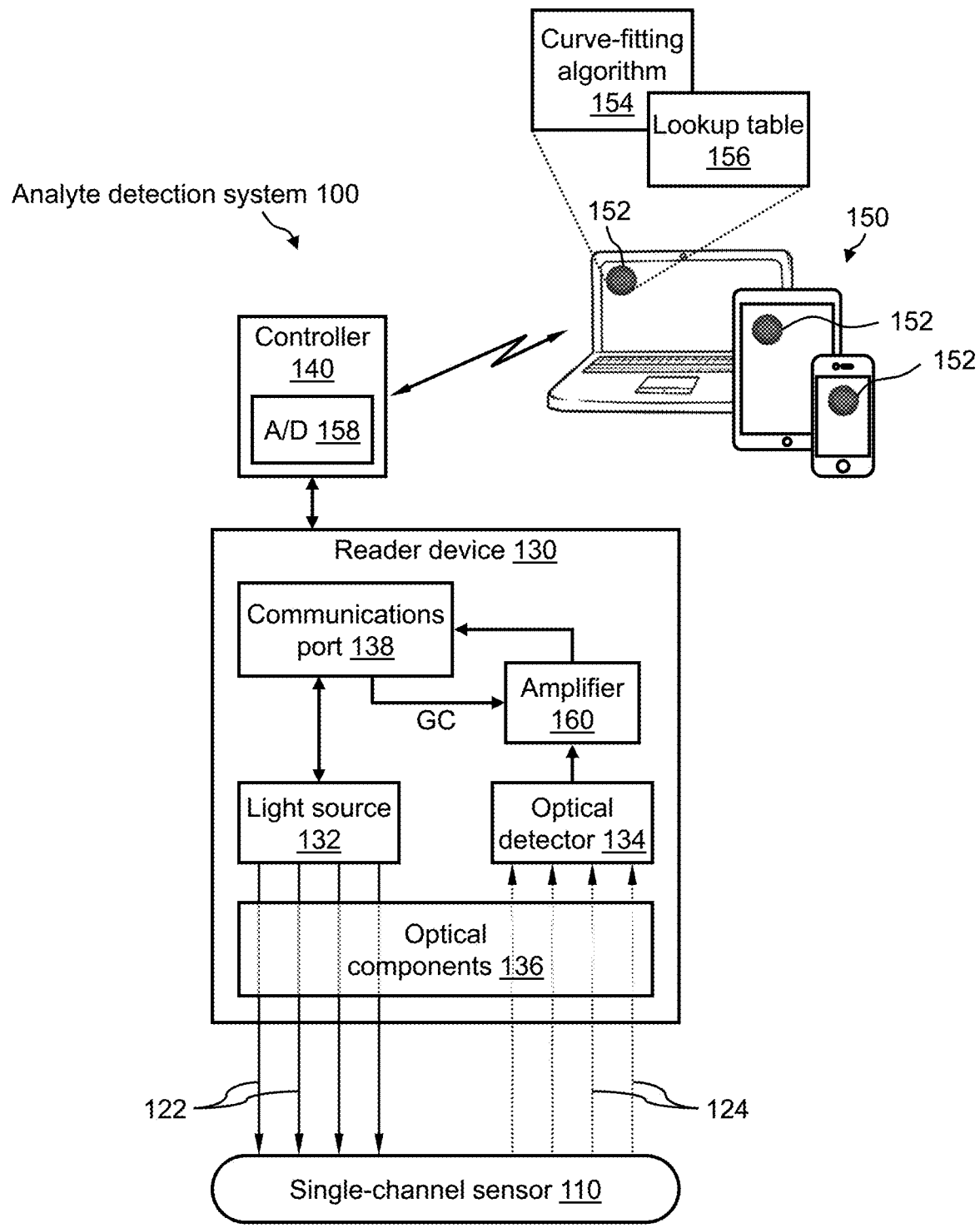
FIG. 3 illustrates a schematic block diagram of a reader device, according to an embodiment.

FIG. 3 is a schematic block diagram of a of reader device 130 of the presently disclosed analyte detection system 100, according to an embodiment. In this embodiment, the processing capability of analyte detection system 100 is external to reader device 130 that is located on the surface of the skin. Namely, a communications link is provided between reader device 130, a controller 140, and a separate computing device 150, wherein controller 140 and/or computing device 150 may be used for processing any information from reader device 130.

In this example, controller 140 may be a separate control board that is arranged between reader device 130 and computing device 150. Similarly stated, controller 140 may be physically and/or logically coupled to or disposed within a housing of the computing device 150, or may be disposed in a break out box or other intermediate location between the reader device 130 and computing device 150. As described in further detail herein, in other embodiments, controller 140, may be physically and/or logically coupled to or disposed within a housing of the reader device 130 such that reader device 130 provides a digital output. Controller 140 includes an analog-to-digital (A/D) converter 158. A/D 158 is used to receive and digitize the analog output of amplifier 160 of reader device 130. For example, A/D 158 can be any suitable A/D converter (e.g., a 12- or 16-bit A/D), and has a sampling rate suitable for measuring the lifetime of the long lifetime dye. Controller 140 can have a wired or wireless connection to reader device 130. Controller 140 can have a wired or wireless connection to computing device 150. Controller 140 can be any standard controller or microprocessor device that is capable of executing (e.g., on a processor) program instructions (e.g., stored in memory). Controller 140 and/or computing device 150 can manage the overall operations of analyte detection system 100.

Computing device 150 may be any type of computing device, such as a desktop computer, a laptop computer, a tablet device, a mobile phone, a smartphone, a smartwatch, and the like. Computing device 150 includes a processor and a memory. A desktop application 152 and/or mobile app 152 can reside on computing device(s) 150 (e.g., stored in memory and/or executing on a processor) and used to process information from reader device 130.

Further, in this example, reader device 130 includes a light source 132, an optical detector 134, certain optical components 136, and a communications port 138. Further, the analog output of optical detector 134 supplies an amplifier 160. Amplifier 160 may be, for example, a standard operational amplifier (OP AMP) that has (1) a bandwidth suitable to capture the output signal of optical detector 134, and (2) an adjustable gain feature. In some embodiments, reader device 130 may include a power source (not shown), such as a battery. In other embodiments, controller 140 and/or computing device 150 supplies power to reader device 130. Reader device 130 is designed to be fitted against the surface of the skin.

Light source 132 is arranged to transmit excitation light 122 from the surface of the skin, through the tissue 105, and to single-channel sensor 110. The excitation light 122 from light source 132 is within the excitation wavelength range of both analyte sensing moieties 118 and reference moieties 120. Accordingly, the fluorescent dyes of both analyte sensing moieties 118 and reference moieties 120 are excited simultaneously. Suitable light sources may include, but are not limited to, lasers, semi-conductor lasers, light emitting diodes (LEDs), and organic LEDs. In some embodiments the light source 132 may be a single light source configured to simultaneously excite both analyte sensing moieties 118 and reference moieties 120. In other embodiments, the reader device 130 can include multiple light sources 132 each having the same, substantially the same, or overlapping illumination spectrums such that the multiple light sources 132 are collectively configured to excite both analyte sensing moieties 118 and reference moieties 120 simultaneously.

Optical detector 134 is configured to detect emission light 124 from analyte sensing moieties 118 and reference moieties 120 of single-channel sensor 110 and through tissue 105. Optical detector 134 is configured to detect emission light 124 in the emission wavelength range of both analyte sensing moieties 118 and reference moieties 120. Accordingly, optical detector 134 detects emission light 124 from both analyte sensing moieties 118 and reference moieties 120 simultaneously. Suitable detectors may include, but are not limited to, photodiodes, complementary metal-oxide-semiconductor (CMOS) detectors, charge-coupled device (CCD) detectors, and silicon photomultipliers (SiPM). In some embodiments the detector 134 may be a single detector configured to detect light 124 in the emission wavelength range of both analyte sensing moieties 118 and reference moieties 120 simultaneously. In other embodiments, reader device 130 can include multiple detectors 134 each having substantially the same, substantially the same, or overlapping detection spectrums such that the multiple detectors 134 are collectively configured to detect light 124 in the emission wavelength range of both analyte sensing moieties 118 and reference moieties 120 simultaneously.

Optical detector 134 can be filtered (e.g., with dichroic filters, band-pass filters, or other suitable filters) such that light outside the detection spectrum of the optical detector 134 and/or the emission spectrum(s) of the analyte sensing moieties 118 and the reference moieties 120 are attenuated or blocked before reaching the optical detector 134. Optical filters are one example of optical components 136. However, optical components 136 may include any other types of components needed in reader device 130. In some embodiments, the detector 134 may include a single filter operable to pass light having wavelengths within the excitation spectrum and/or the emission spectrum of the sensing moieties 118 and reference moieties 120. Similarly stated, in some embodiments, light having wavelengths outside the excitation spectrum and/or the emission spectrum of the sensing moieties 118 and reference moieties 120 can be attenuated or blocked before it leaves light source 132 and/or illuminates detector 134, respectively. In other embodiments, each light source 132 can be filtered such that only light within the excitation spectrum of sensing moieties 118 and reference moieties 120 is emitted from the reader device 130 while each optical detector 134 can be filtered such that only light within the emission spectrum of sensing moieties 118 and reference moieties 120 can reach optical detectors 134.

Communications port 138 can facilitates a communications link to light source 132 optical detector 134, and/or processor(s) and/or memory of the reader device 130 (not shown in FIG. 3). For example, communications port 138 can be a wired communications port, such as a USB port. Using communications port 138, the separate computing device 150 may be communicatively connected to light source 132 and optical detector 134 of single-channel sensor 110. Namely, computing device 150 may be used to activate light source 132 and to collect information from optical detector 134, wherein optical detector 134 converts optical signals received from single-channel sensor 110 to an electrical signal output.

Computing device 150 may use desktop application 152 or mobile app 152 to process any information from single-channel sensor 110. Namely, desktop application 152 or mobile app 152 may include any software and/or hardware components for processing any information from single-channel sensor 110. In one example, desktop application 152 or mobile app 152 includes a curve-fitting algorithm 154 and a lookup table 156.

The optical signal (i.e., emission light 124) reaching the optical detector 134 includes both a short-lifetime dye component and a long-lifetime dye component. Further, the intensity of the short-lifetime dye component may be orders of magnitude greater than the intensity of the long-lifetime dye component. For example, the intensity of the short-lifetime dye component can be 10 to 100 times greater than the intensity of the long-lifetime dye component. The output of optical detector 134 supplies a single amplifier 160 that can process both the short-lifetime dye component and the long-lifetime dye component, which can be challenging because of the very different intensities. Accordingly, reader device 130 of analyte detection system 100 includes a fast gain control feature for amplifier 160. For example, controller 140 generates and sends a gain control (GC) signal to amplifier 160.

The timing of the GC signal can be, for example, based on the control of light source 132. Namely, when light source 132 is activated (corresponding in time with the short-lifetime dye component) the GC signal sets amplifier 160 to a certain low gain setting (e.g., Gain=1). Then, when light source 132 is deactivated (corresponding in time with the long-lifetime dye component) the GC signal sets amplifier 160 to a certain higher gain setting (e.g., Gain=10 or 100). Similarly stated, in some embodiments, the GC signal can be sent simultaneously with deactivating the light source 132 and/or after a period of time corresponding with the fluorescence lifetime of the short-lifetime dye component. In this way, the output range of amplifier 160 can be adjusted in a manner that is easier to process.

Figure 4:
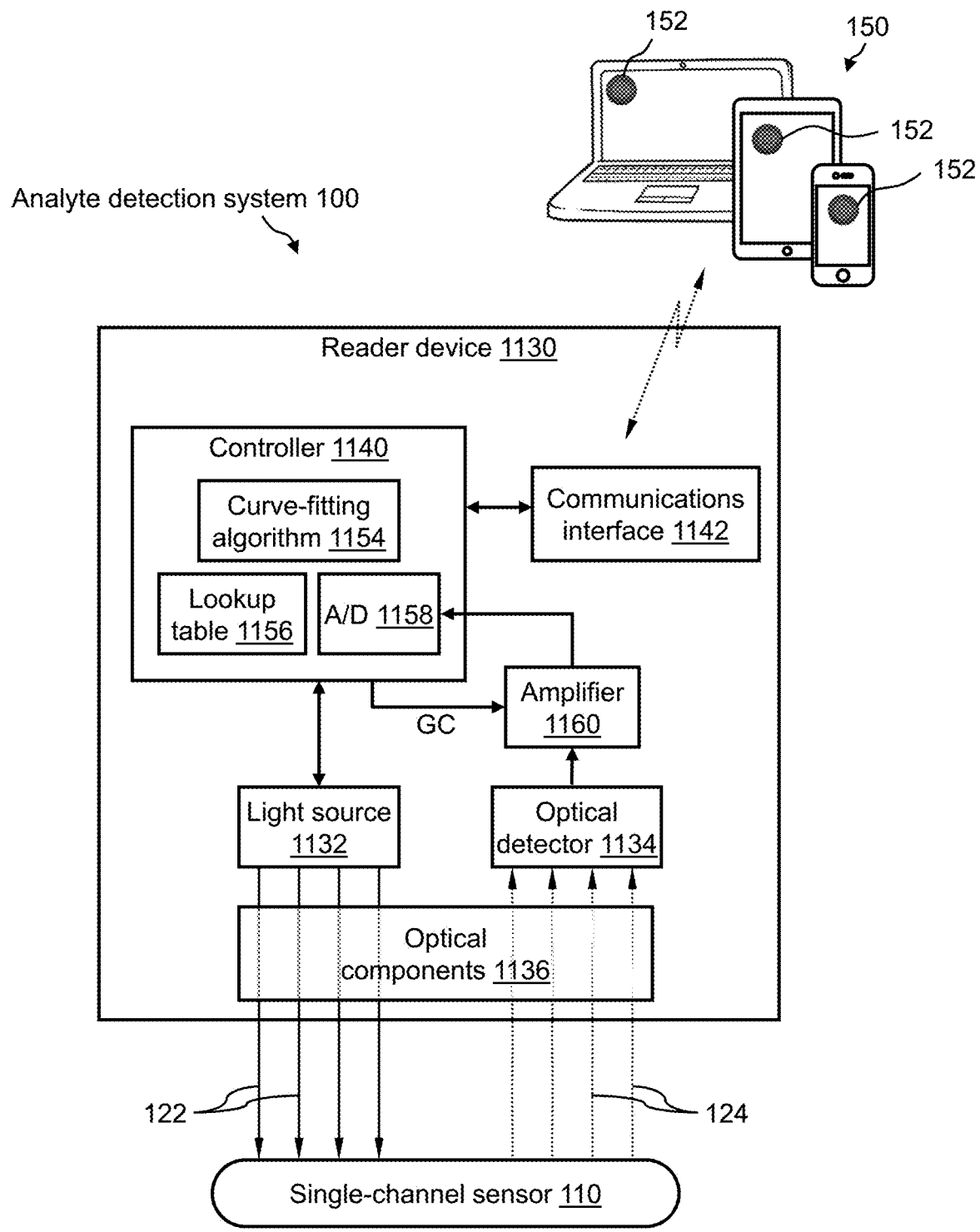
FIG. 4 illustrates a schematic block diagram of a reader device, according to another embodiment.

FIG. 4 is a schematic block diagram of an alternative embodiment of the reader device 130 and described above with reference to FIG. 1-3. In this embodiment, the processing capability of analyte detection system 100 is on board reader device 1130 that is configured to be located on the surface of the skin, rather than on a separate computing device 1150. Reader 1130 includes a controller 1140 that includes a curve fitting algorithm 1154, a look up table 1156, and an A/D converter 1158, each of which can be structurally and/or functionally similar to the controller 140, the curve fitting algorithm 154, the look up table 156, and/or the A/D converter 158, respectively, as shown and described above. Reader 1130 further includes an amplifier 1160, a light source 1132, an optical detector 1134, and optical component(s) 1136, each of which can be structurally and/or functionally similar to the amplifier 160, the light source 132, the optical detector 134, and/or optical component(s) 136, respectively, shown and described above. Communications interface 1142 can further be structurally and/or functionally similar to communications interface 142 shown and described above.

In this embodiment, in addition to light source 132, optical detector 134, optical components 136, and amplifier 160 as described in FIG. 3, reader device 1130 includes a controller 1140 and a communications interface 1142. Namely, in this embodiment, controller 1140 is now an onboard controller (e.g., located within a housing of reader device 1130) rather than a separate control board. Controller 1140 includes A/D 1158, which is now onboard reader device 1130 such that A/D 1158 provides a digital output directly from reader device 1130.

Further, in this example, controller 1140 includes any software and/or hardware components (e.g., a processor and/or a memory) for processing any information from single-channel sensor 1110. For example, curve-fitting algorithm 1154 and lookup table 1156 may reside at controller 1140 of reader device 1130 rather than at the separate computing device 150.

Again, controller 1140 may be any standard controller or microprocessor device that is capable of executing program instructions (e.g., stored in memory). Controller 1140 manages the overall operations of single-channel sensor 110 and/or analyte detection system 100.

Communications interface 1142 may be any wired and/or wireless communication interface for connecting to a network (not shown) and by which information may be exchanged with other devices (e.g., computing device 150) connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, cellular networks, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. In one example, communications interface 1142 is Bluetooth® technology for communicating with a mobile app on a mobile device.

Referring still to FIG. 3 and FIG. 4, curve-fitting algorithm 154, 1154 may be used to:

(1) render a waveform of the optical signal captured by optical detector 134, 1134 of reader device 130, 1130, (2) determine the short-lifetime component of the optical signal (see FIGS. 5, 6, 7), (3) determine the long-lifetime component of the optical signal (see FIGS. 5, 6, 7), (4) calculate an intensity ratio, which is the ratio of the short-lifetime intensity to the long-lifetime intensity. Again, the intensity ratio can be used to normalize the analyte value for dynamic and tissue optics variations that occur in the tissue between single-channel sensor 110 and the surface of the skin where reader device 130, 1130 is located. In so doing, an accurate analyte value can be determined, and/or (5) correlate the intensity ratio to an analyte value using lookup table 156, 1156. Accordingly, the contents of lookup table 156, 1156 is a list of intensity ratio values and their corresponding analyte values.

Curve-fitting algorithm 154, 1154 may calculate the intensity ratio, which is the ratio of the short-lifetime intensity to the long-lifetime intensity, using, for example, Equations 1 through 4 below, which is described in more detail hereinbelow with reference to the method of FIG. 8.

Short-lifetime signal intensity: $I_{SLI}=P_{ex}[T_{leak}+T_{af}+T_{ex}\beta_{SL}T_{em}]$     [Equation 1]

where $I_{SLI}$ is short-lifetime intensity;

$P_{ex}$ is excitation light power (or intensity);

$T_{leak}$ is diffuse reflectance filter leakage;

$T_{af}$ is tissue autofluorescence;

$T_{ex}$ is excitation transmission factors;

$\beta_{SL}$ is sensor fluorescence efficiency; and $T_{em}$ is emission transmission factors.

In Equation 1, β relates to the selected analyte die. So for different analytes, β changes. By contrast, the transmission factors T are those factors that are not sensitive to the presence or amount of the target analyte. Further, the transmission factors T are unitless factors. For example, $T_{leak}$ may be 0.01, which means that 1% of the excitation light leaks back to the detector. $T_{af}$ may be 0.05, which means that 5% of the excitation light comes back to the detector as autofluorescence. $T_{ex}$ and $T_{em}$ are the transmission factors of the light source that propagate through tissue to the detector.

Long-lifetime signal intensity: $I_{LLI}=P_{ex}[T_{ex}\beta_{LL}T_{em}]$ [Equation 2]

where $I_{LLI}$ is long-lifetime intensity;
$P_{ex}$ is excitation light power (or intensity);
$T_{ex}$ is excitation transmission factors;
$B_{LL}$ is sensor fluorescence efficiency; and
$T_{em}$ is emission transmission factors.

In Equation 2, β relates to the selected reference die. By contrast, the transmission factors T are those factors that are not sensitive to the selected reference dye.

Further, in Equations 1 and 2, $T_{ex}$ and $T_{em}$ are can be the same because the short-lifetime analyte-sensing dye and long-lifetime reference dye are in the same wavelength range. Therefore, when the Intensity Ratio is calculated in Equation 4, $T_{ex}$ and $T_{em}$ cancel out.

Short-lifetime background light: $I_{SLIb}=P_{ex}[T_{leak}+T_{af}]b$ [Equation 3]

where $I_{SLIb}$ is short-lifetime background intensity;
$P_{ex}$ is excitation light power (or intensity);
$T_{leak}$ is diffuse reflectance filter leakage; and
$T_{af}$ is tissue autofluorescence.
[Equation 4] Intensity Ratio:

$$I_{ratio} = \frac{[I_{SLI} - I_{SLIb}]}{I_{LLI}} = \frac{\beta_{SLI}}{\beta_{LLI}}$$

where $I_{ratio}$ is intensity ratio.

The intensity ratio is proportional to the analyte level, which may be changing. It is desirable that the calculated analyte level be sensitive to β only. Conversely, it is not desirable that the calculated analyte level be effected by the transmission factors T. For example, the depth of tissue can change, which effects the reading, yet the intensity ratio stays the same. Accordingly, using the intensity ratio removes the sensitivity to the dynamic and tissue optics variations that occur in the tissue between single-channel sensor 110 and the surface of the skin where reader device 130, 1130 is located.

Figure 5:
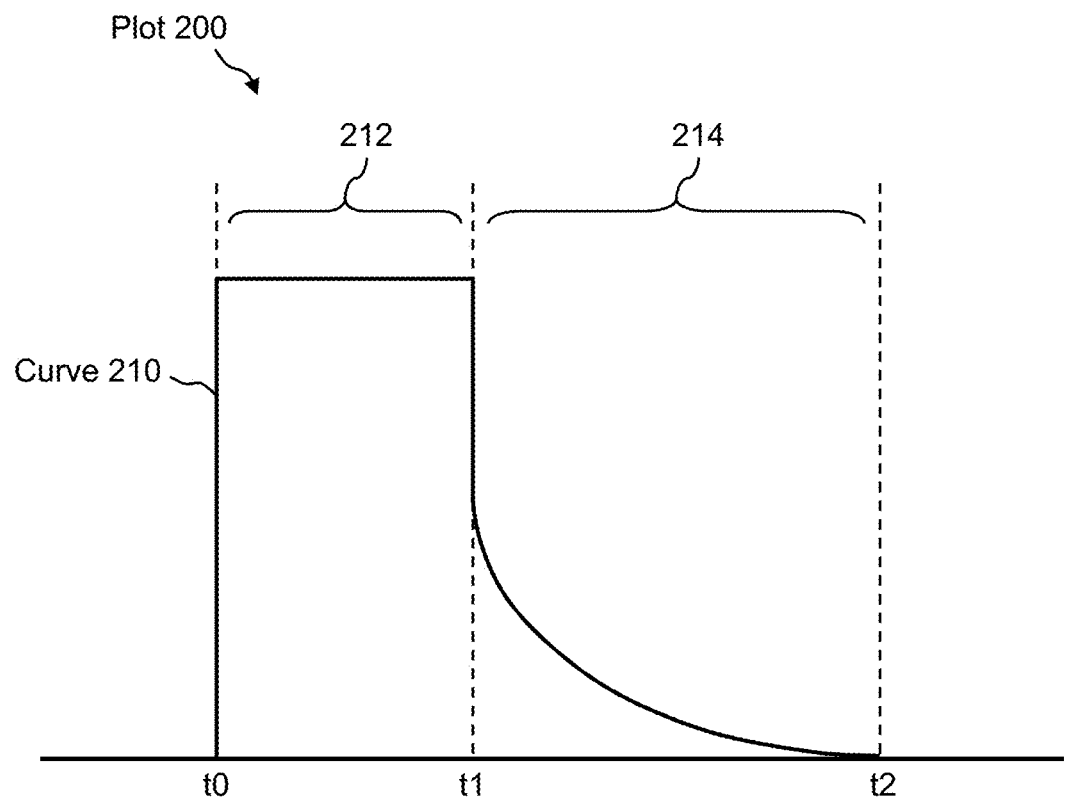
FIG. 5, FIG. 6, and FIG. 7 show example plots of the emission intensity of the single-channel sensor of analyte detection system, including a short-lifetime dye and a long-lifetime dye components, according to embodiments.
Figure 6:
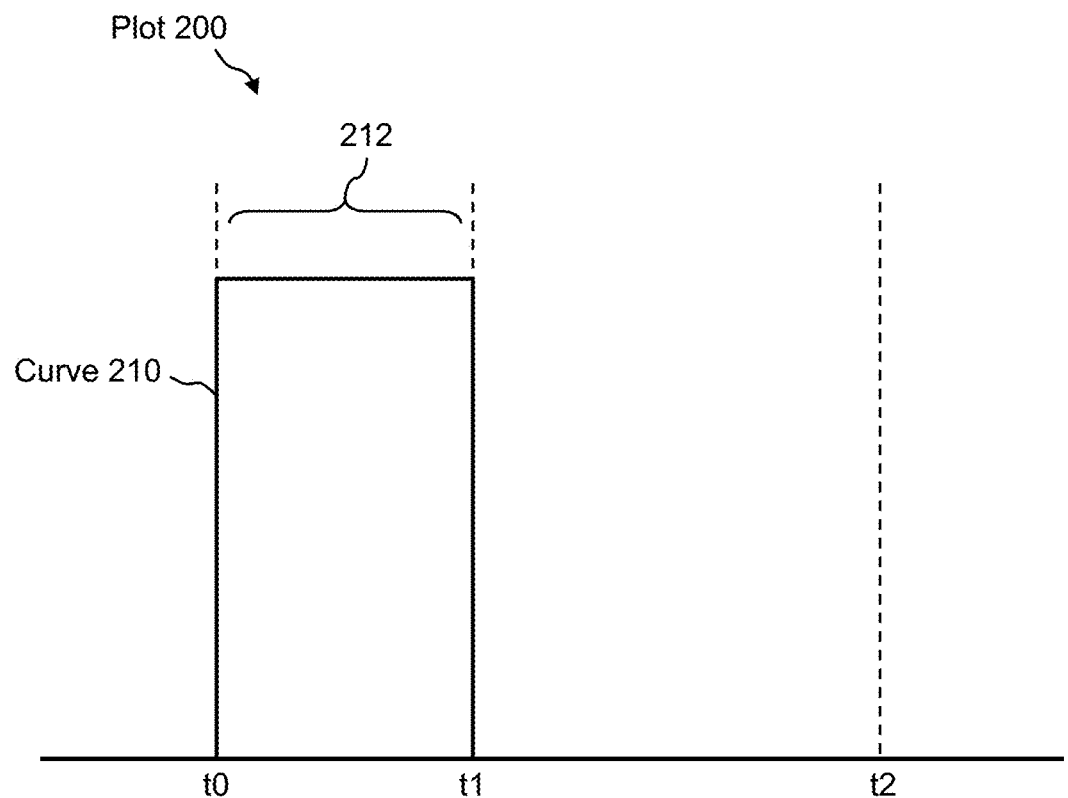
Figure 7:
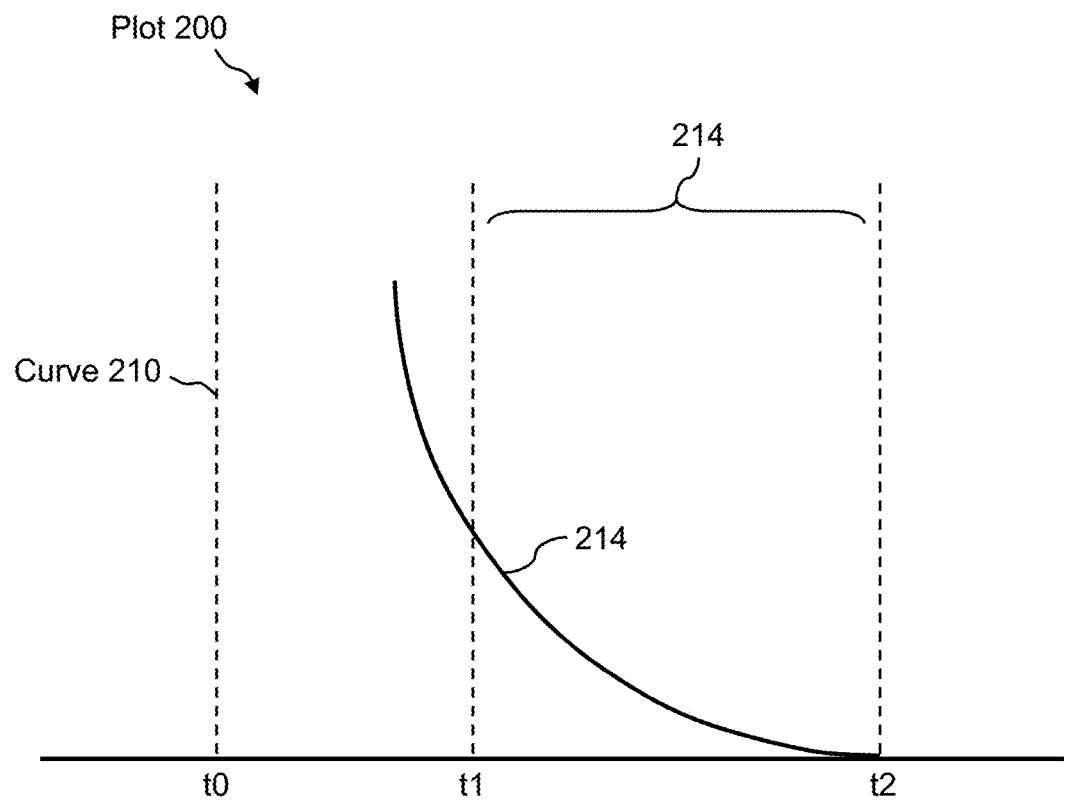

FIG. 5 is a plot 200 of the emission intensity of single-channel sensor 110 of the presently disclosed analyte detection system 100, wherein plot 200 indicates the combination of both the short-lifetime dye component and the long-lifetime dye component of the optical signal returned from single-channel sensor 110. Namely, a curve 210 indicates the emission intensity of the optical signal returned from single-channel sensor 110, wherein the optical signal includes emission from both analyte sensing moieties 118, which is the short-lifetime analyte-sensing dye, and reference moieties 120, which is the long-lifetime reference dye. In curve 210, a portion 212 indicates the short-lifetime dye component (e.g., about ≤50 ns lifetime) of curve 210. In curve 210, a portion 214 indicates the long-lifetime dye component (e.g., about ≥1 μs lifetime) of curve 210. Further to the example, FIG. 6 shows the short-lifetime dye component only (i.e., portion 212 only) of curve 210 in plot 200. By contrast, FIG. 7 shows the long-lifetime dye component only (i.e., portion 214 only) of curve 210 in plot 200. Given the scale of plot 200 shown in FIG. 5, FIG. 6, and FIG. 7, portion 212 of curve 210 substantially corresponds to the period of time that light source 132 of reader device 130 is turned on, which is the period of time that both analyte sensing moieties 118 and reference moieties 120 are illuminated. Plot 200 of FIG. 5, FIG. 6, and FIG. 7 shows that the decay time of the long-lifetime dye is significantly longer than the decay time of the short-lifetime dye.

Referring now to FIG. 3, FIG. 4, and FIG. 5 and with respect to the gain control feature of analyte detection system 100, using the GS signal, the gain of amplifier 160 can be set, for example, to a pre-determined and/or dynamic low gain value (e.g., 1) at portion 212 of curve 210, then the gain of amplifier 160 can be set to a pre-determined and/or dynamic high gain value (e.g., to 10 or 100) at portion 214 of curve 210. In this example, the GC signal (not shown) switches at about t1. Further, the GC signal switches rapidly (e.g., about 1 μs transition time) with respect to the length of the short-lifetime dye component and the long-lifetime dye component (e.g., about 50 μs to about 200 μs).

Figure 8:
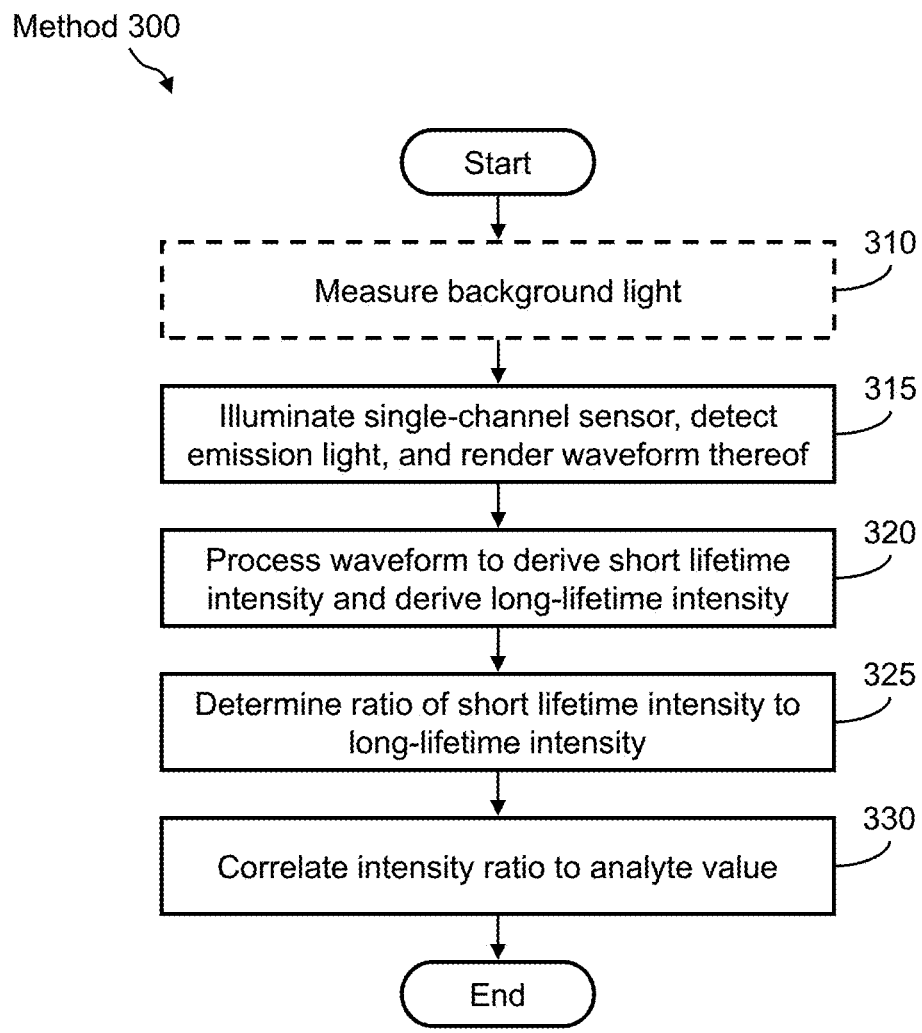
FIG. 8 illustrates a flow diagram of a method of using an analyte detection system to determine an analyte value, according to an embodiment.

FIG. 8 is a flow diagram of a method 300 of using the presently disclosed analyte detection system 100 to determine an analyte value (e.g., analyte concentration), according to an embodiment. Method 300 may include, but is not limited to, the following events.

Optionally, at 310, the background light with respect to single-channel sensor 110 is measured. In one example, reader device 130 can be placed on the skin at a location away from single-channel sensor 110. Accordingly, at this location there is no short-lifetime analyte-sensing dye nor long-lifetime reference dye present. Then, light source 132 is pulsed and an optical signal is captured via optical detector 134. Then, using this information, curve-fitting algorithm 154 may be used to calculate the short-lifetime background light according to Equation 3 above.

At 315, reader device 130 is be placed on the skin in close proximity to single-channel sensor 110. Similarly stated, the reader device 130 can be placed on the surface of skin immediately above or in the vicinity of the single channel sensor 110. Then, single-channel sensor 110 is illuminated by pulsing light source 132. Then, emission light 124 from analyte sensing moieties 118, which is the short-lifetime analyte-sensing dye, and/or reference moieties 120, which is the long-lifetime reference dye, is captured via optical detector 134. Then, curve-fitting algorithm 154 may be used to render a waveform of the optical signal captured by optical detector 134. An example of the waveform is curve 210 shown in plot 200 of FIG. 5.

At 320, the waveform determined at 315 is processed to derive the short-lifetime intensity and the long-lifetime intensity. For example, curve-fitting algorithm 154 may be used derive the short-lifetime intensity according to Equation 1 above. Also, curve-fitting algorithm 154 may be used to derive the long-lifetime intensity according to Equation 2 above.

At 325, the intensity ratio, which is the ratio of the short-lifetime signal to the long-lifetime signal, is determined. For example, using curve-fitting algorithm 154, the intensity ratio is determined according to Equation 4 above. Namely, using Equation 4, the short-lifetime background calculated at 310 is subtracted from the short-lifetime intensity calculated at 320 and then the intensity ratio is determined.

At 330, the intensity ratio is correlated to an analyte value (e.g., an analyte concentration). For example, curve-fitting algorithm 154 may use lookup table 156 to correlate the calculated intensity ratio to an analyte value or analyte concentration. In an example in which the analyte is glucose, lookup table 156 may indicate that a given intensity ratio correlates to a given glucose concentration.

Optionally, at 330, the intensity ratio calculated at 325 plus a temperature measurement can be input to an analyte calibration lookup table based on in vitro reference data that may be used to convert the intensity ratio and the temperature to an analyte concentration.

Experimental Hydrogels

Hydrogels were constructed using acrylate-based monomers and a thermal initiator. As the short-lifetime component, a boronic-acid based glucose-sensitive monomeric dye was added to the pre-polymer mix at a concentration of 0.01 mMolar. As the long-lifetime component, an inorganic phosphor based on chromium(III)-doped yttrium aluminum borate (Cr-YAB) as discussed in Borisov et al., "Preparation and Characterization of Chromium(III)-Activated Yttrium Aluminum Borate: A New Thermographic Phosphor for Optical Sensing and Imaging Ambient Temperatures," The Journal of Physical Chemistry C; 2010, 114, 9118-9124," which is hereby incorporated by reference in its entirety, was added to the prepolymer mix at a concentration of 50 mg/mL. The prepolymer mix was injected in between two glass plates separated by a 0.015" thick spacer, and then heated at 45° C. for 4 hours. The resulting hydrogel slab was removed from the mold and washed with pH 7.4 PBS.

The dye concentrations were selected to make the short-lifetime intensity (SLI) and long-lifetime intensity (LLI) signals comparable in order to test this technique. However, these concentrations may be tuned to increase glucose sensitivity.

For measurements, skin phantom layers (cured silicone with titanium dioxide to simulate tissue scattering) were placed on top of the analyte-sensing hydrogel. An optical reader was placed on top of the skin phantom layers. Varying the skin phantom layers between the reader and the hydrogel-based sensor, was done to simulate changing tissue depth.

For both the glucose sensor dye and the reference dye, excitation is performed at 630 nm and emission is collected at ~700 nm by the optical reader.

Figure 9A:
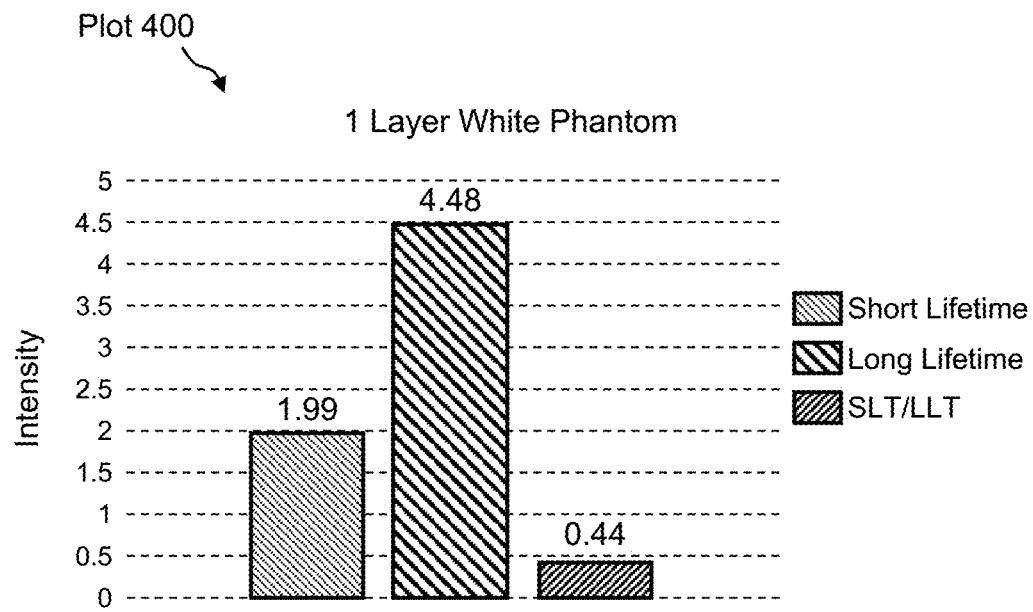
FIG. 9A and FIG. 9B show plots of the results of certain experiments with respect to demonstrating the ratio of short-lifetime intensity to long-lifetime intensity.
Figure 9B:
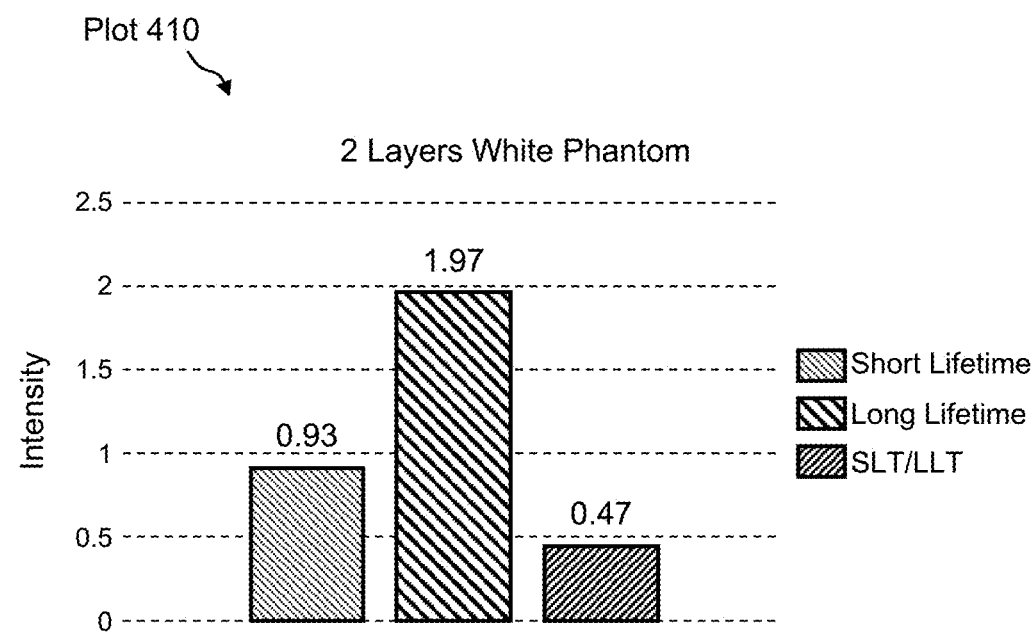

Referring now to FIG. 9A, a plot 400 shows the results using 1 layer of white phantom, wherein SLI=1.99, LLI=4.48, and intensity ratio=0.44. Referring now to FIG. 9B, a plot 410 shows the results using 2 layers of white phantom, wherein SLI=0.93, LLI=1.97, and intensity ratio=0.47. In this example, as depth is varied, the absolute intensity of the short lifetime dye and the long lifetime dye by about 2×, but the intensity ratio remains approximately constant. In general, it is demonstrated here that the ratio of SLI to LLI can provide a correction for intensity variations due to changes in signal intensity, which can be influenced by, for example the depth of tissue between the sensor and the reader.

Figure 10:
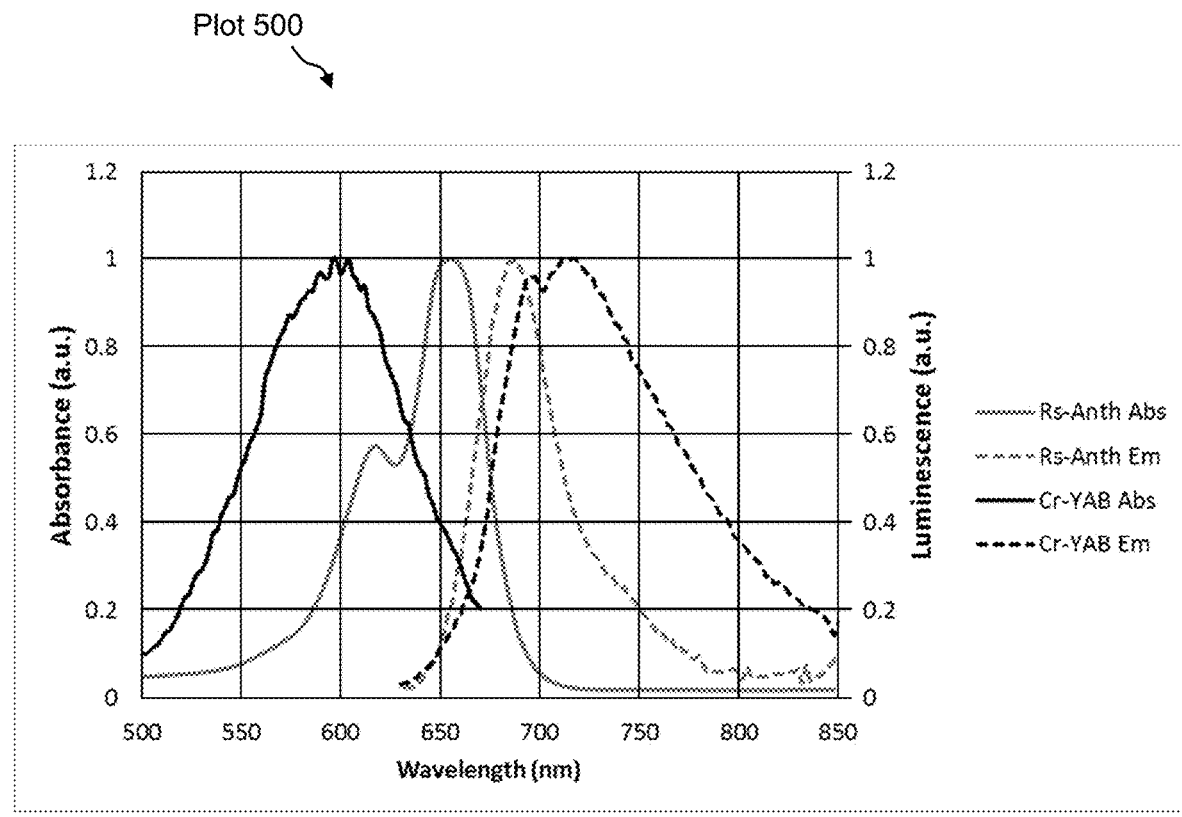
FIG. 10 shows a plot of an example of the overlapping absorbance and emission spectra of a short-lifetime and long-lifetime dye.

FIG. 10 shows a plot 500 of an example of the overlapping absorbance and emission spectra of a short-lifetime and long-lifetime dye. The information shown in plot 500 demonstrates that a single illumination source and a single common detector can be used in reader device 130 of the presently disclosed analyte detection system 100.

In summary and referring now to FIG. 1 through FIG. 10, the presently disclosed analyte detection system 100 and method 300 provide a highly quantitative analyte measurement wherein the sensitivity to variables other than the analyte is reduced or substantially eliminated as compared with conventional sensing methods. Namely, as compared with conventional sensing methods, analyte detection system 100 and method 300 provide an analyte measurement that has little or no sensitivity to, for example, motion artifacts (e.g., reader position), tissue artifacts (e.g., depth, pressure), oxygen artifacts (e.g., tissue oxygenation), and the like in order to make the analyte measurement more quantitative. Further, an advantage of analyte detection system 100 and method 300 is that because the short-lifetime analyte-sensing dye and the long-lifetime reference dye emit in the same or overlapping spectrums, more accurate measurements are possible as compared with an analyte-sensitive dye and a reference dye that have different and/or non-overlapping spectrums.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Some embodiments described herein refer to short-lifetime dye and long-lifetime dye. It should be understood that "short" and "long" are relative descriptors used to describe the short-lifetime dye by reference to the long-lifetime dye and vice versa. Similarly stated, although some embodiments provide details of specific lifetimes of short-lifetime dyes and/or long-lifetime dyes, the terms "short" and "long" do not require that the lifetime of the respective dye be below or above any particular threshold.

Some embodiments described herein refer to spectrums being the same, substantially the same, and/or overlapping. Two spectrums can be considered overlapping if, for example, a 30 nm band exists in which an intensity of each spectrum is at least 10% of the peak intensity for that spectrum. In some embodiments, light emitted from a sensor can pass through a 30 nm wide band pass filter before being received by a detector. A signal that has an intensity within that band that is at least 10% of the peak intensity for that signal can be reliably measured by the detector. Therefore, two signals have "overlapping" spectrums if a 30 nm wide band pass filter can be selected that will pass a band of each spectrum in which an intensity of each signal is at least 10% of the maximum intensity for that spectrum. Similarly, two spectrums can be considered "the same" if a 30 nm band exists in which an intensity of each spectrum is at least 75% of the peak intensity for that spectrum and two spectrums can be considered "substantially the same" if a 30 nm band exists in which an intensity of each spectrum is at least 50% of the peak intensity of that spectrum. In other embodiments, wider or narrower band-pass (or other suitable filters) can be used, and spectrums of signals can be considered to be the same, substantially the same, or overlapping if the signals can be reliably measured after passing through the filter.

Although the foregoing subject matter has been described in some detail by way of illustration and example for purposes of clarity of understanding, it will be understood by those skilled in the art that certain changes and modifications can be practiced within the scope of the appended claims. While various embodiments have been described above, it should be understood that they have been presented by way of example only, and not limitation. Although various embodiments have been described as having particular features and/or combinations of components, other embodiments are possible having a combination of any features and/or components from any of embodiments where appropriate. For example, although embodiments described herein generally reference short-lifetime analyte sensing dyes and long-lifetime reference dyes, it should be understood that other embodiments can include long-lifetime analyte sensing dyes and short-lifetime reference dyes. As another example, it should be understood that sensors described herein can include any number of sensing moieties. As an illustration, a sensor can include a short-lifetime glucose sensing dye, a long-lifetime reference dye associated with the short-lifetime glucose sensing dye, and a long-lifetime oxygen sensing dye without an associated reference dye. Such a long-lifetime oxygen sensing dye may have a different emission spectrum than the short-lifetime glucose sensor and the long-lifetime reference dye.

Where methods and/or schematics described above indicate certain events occurring in certain order, the ordering of certain events may be modified. Additionally certain events may be performed concurrently in parallel processes when possible, as well as performed sequentially. While the embodiments have been particularly shown and described, it will be understood that various changes in form and details may be made.

Some embodiments described herein relate to methods. It should be understood that such methods may be computer-implemented (e.g., performed by a processor executing code stored in memory). For example some methods described herein may be implemented by the computing device 150 and/or the reader device 1130 shown and described above.

It should therefore be understood that devices described herein can include a processor or other module configured to store and execute program code, such as Application-Specific Integrated Circuits (ASICs), Programmable Logic Devices (PLDs), Read-Only Memory (ROM) and Random-Access Memory (RAM) devices. Devices shown and described herein can also include memory, also referred to as a non-transitory computer-readable medium. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules. The computer-readable medium (or processor-readable medium) is non-transitory in the sense that it does not include transitory propagating signals per se (e.g., a propagating electromagnetic wave carrying information on a transmission medium such as space or a cable). The media can store or be operable to store computer code (also can be referred to as code) that is executable by the processor to cause the computer implemented method to be performed.

That which is claimed:

1. A system, comprising:
    a sensor, including:
        an analyte-sensing dye configured to emit an analyte-dependent optical signal in the presence of an analyte, the analyte-dependent optical signal having an analyte-dependent spectrum and a first duration; and
        a reference dye configured to emit an analyte-independent optical signal having an analyte-independent spectrum and a second duration, the analyte-dependent spectrum and the analyte-independent spectrum overlapping, the second duration exceeding the first duration; and
    a reader, including:
        a light source configured to emit an illumination signal configured to excite the analyte-sensing dye and the reference dye, the analyte-sensing dye and the reference dye configured to emit the analyte-dependent optical signal and the analyte-independent optical signal, respectively, in response to being excited by the illumination signal;
        a detector configured to detect the analyte-dependent optical signal and the analyte-independent optical signal;
        an amplifier having variable gain, the amplifier configured to process a signal received during a first time period that is associated with the analyte-dependent optical signal with a first gain to produce a first processed signal, the amplifier configured to process a signal received during a second time period that is associated with the analyte-independent signal with a second gain different from the first gain to produce a second processed signal, the second time period being after the first time period; and
        a processor configured to determine at least one of a concentration or a quantity of the analyte based on a ratio of the first processed signal and the second processed signal.

2. The system of claim 1, wherein the illumination signal has a spectrum configured to simultaneously excite the analyte-sensing dye and the reference dye.

3. The system of claim 1, wherein the light source is a single light source configured to emit a single illumination signal configured to simultaneously excite the analyte-sensing dye and the reference dye.

4. The system of claim 1, wherein the detector is a single detector configured to detect each of the analyte-dependent optical signal and the analyte-independent optical signal.

5. The system of claim 1, wherein:
the sensor is configured to be implanted in tissue of a body; and
the reader is configured to be disposed outside the body, the sensor and the reader not being physically coupled.

6. The system of claim 1, wherein the reader includes a filter disposed between the light source and the sensor, all light emitted from the reader passing through the filter.

7. The system of claim 1, wherein the reader includes a filter disposed between the detector and the sensor, all light entering the reader passing through the filter.

8. The system of claim 1, wherein the second duration is at least an order of magnitude greater than the first duration.

9. The system of claim 1, wherein the reference dye is configured to emit the analyte-independent optical signal with an intensity that is insensitive to a chemical environment in which the reference dye is disposed.

10. The system of claim 1, wherein the first duration is less than 50 nanoseconds.

11. The system of claim 1, wherein the second duration is greater than 1 microsecond.

12. The system of claim 1, wherein:
the first duration is less than 50 nanoseconds; and
the second duration is greater than 1 microsecond.

13. The system of claim 1, wherein the analyte is at least one of oxygen, glucose, lactate, carbon dioxide, $H^+$, or $OH^-$.

14. The system of claim 1, wherein:
the analyte-sensing dye is a first analyte-sensing dye configured to emit a first analyte-dependent optical signal in the presence of a first analyte; and
the analyte-dependent optical signal is a first analyte-dependent optical signal having a first analyte-dependent spectrum, the system further comprising:
a second analyte-sensing dye configured to emit a second analyte-dependent optical signal in the presence of a second analyte, the second analyte-dependent optical signal having a second analyte-dependent spectrum different from the first analyte-dependent spectrum.

15. The system of claim 1, wherein the sensor is configured to be implanted in tissue of a body.

16. The system of claim 1, wherein:
the sensor is configured to be implanted in tissue of a body; and
the analyte-sensing dye is configured to emit the analyte-dependent optical signal in the presence of the analyte within blood or interstitial fluid of the tissue.

17. A method, comprising:
illuminating a sensor with an illumination signal to simultaneously excite an analyte-dependent dye and an analyte-independent dye such that the analyte-dependent dye emits an analyte-dependent optical signal having a first duration simultaneously with the analyte-independent dye emitting an analyte-independent optical signal having a second duration longer than the first duration, a spectrum of the analyte-independent optical signal overlapping a spectrum of the analyte-dependent optical signal;
detecting the analyte-dependent optical signal during a first time period;
processing a signal associated with the analyte-dependent optical signal with an amplifier at a first gain;
detecting an analyte-independent optical signal during a second time period after the first time period;
processing a signal associated with the analyte-independent optical signal with the amplifier at a second gain higher than the first gain; and
determining at least one of a quantity or a concentration of an analyte based on a ratio of the signal associated with the analyte-dependent optical signal processed with the first gain and the signal associated with the analyte-independent optical signal processed with the second gain.

18. The method of claim 17, wherein the illumination signal is emitted from is a single light source configured to emit a single illumination signal configured to simultaneously excite the analyte-sensing dye and the reference dye.

19. The method of claim 17, wherein a spectrum of the analyte-dependent optical signal is the same as a spectrum of the analyte-independent optical signal.

20. The method of claim 17, wherein the analyte-dependent optical signal and the analyte-independent optical signal are detected by the same detector.

* * * * *